United States Patent
Shimizu

(10) Patent No.: US 10,696,616 B2
(45) Date of Patent: Jun. 30, 2020

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

(21) Appl. No.: 16/334,642

(22) PCT Filed: May 15, 2018

(86) PCT No.: PCT/JP2018/018647
§ 371 (c)(1),
(2) Date: Mar. 19, 2019

(87) PCT Pub. No.: WO2019/220522
PCT Pub. Date: Nov. 21, 2019

(65) Prior Publication Data
US 2020/0115310 A1 Apr. 16, 2020

(51) Int. Cl.
*C07C 51/44* (2006.01)
*C07C 51/12* (2006.01)

(52) U.S. Cl.
CPC ............. *C07C 51/44* (2013.01); *C07C 51/12* (2013.01)

(58) Field of Classification Search
CPC ................................ C07C 51/12; C07C 51/44
USPC ........................................................ 562/519
See application file for complete search history.

(56) References Cited

U.S. PATENT DOCUMENTS

| | | | |
|---|---|---|---|
| 4,204,915 A | 5/1980 | Kurata et al. | |
| 5,371,286 A | 12/1994 | Blay et al. | |
| 5,723,660 A | 3/1998 | Morimoto et al. | |
| 6,617,472 B1 | 9/2003 | Thiebaut et al. | |
| 7,683,212 B2 * | 3/2010 | Kojima ................. | B01J 23/464 562/519 |
| 9,006,483 B2 | 4/2015 | Shimizu et al. | |
| 9,540,304 B2 | 1/2017 | Liu et al. | |
| 10,183,905 B2 * | 1/2019 | Shimizu ................... | C01B 3/16 |
| 2003/0204107 A1 | 10/2003 | Daniel et al. | |
| 2004/0133039 A1 | 7/2004 | Zeyss et al. | |
| 2007/0093676 A1 | 4/2007 | Kojima et al. | |
| 2008/0293966 A1 | 11/2008 | Scates et al. | |
| 2008/0293967 A1 | 11/2008 | Scates et al. | |
| 2015/0025270 A1 | 1/2015 | Shimizu et al. | |
| 2016/0137576 A1 | 5/2016 | Liu et al. | |
| 2017/0349521 A1 | 12/2017 | Shimizu et al. | |

FOREIGN PATENT DOCUMENTS

| | | |
|---|---|---|
| EP | 0645362 A1 | 3/1995 |
| EP | 3333147 A1 | 6/2018 |
| JP | 53-116314 A | 10/1978 |
| JP | 4-295445 A | 10/1992 |
| JP | 7-133249 A | 5/1995 |
| JP | 8-67650 A | 3/1996 |
| JP | 2003-502398 A | 1/2003 |
| JP | 2004-513157 A | 4/2004 |
| JP | 2016-117709 A | 6/2016 |
| WO | WO 96/33965 A1 | 10/1996 |
| WO | WO 2006/070632 A1 | 7/2006 |
| WO | WO 2013/137236 A1 | 9/2013 |
| WO | WO 2017/057085 A1 | 4/2017 |
| WO | WO 2018/078924 A1 | 5/2018 |

OTHER PUBLICATIONS

PCT search report for U.S. Appl. No. 16/334,642 (2018).*
International Search Report and Written Opinion of the International Searching Authority for International Application No. PCT/JP2018/018647, dated Jul. 17, 2018.
Extended European Search Report dated Sep. 19, 2019, in European Patent Application No. 18855163.4.

* cited by examiner

Primary Examiner — Yong L Chu
(74) Attorney, Agent, or Firm — Birch, Stewart, Kolasch & Birch, LLP

(57) ABSTRACT

It is intended to provide a method capable of lowering a formic acid concentration in acetic acid product by a simple approach. The method for producing acetic acid according to the present invention comprises at least one step selected from a step that satisfies the following operating condition (i) and a step that satisfies the following operating condition (ii) in an acetic acid production process, and controlling an oxygen concentration in an embodiment satisfying at least one selected from the following (iii) and (iv) for one or more processes:

(i) operating conditions involving a hydrogen partial pressure of less than 500 kPa (absolute pressure), a carbon dioxide partial pressure of less than 70 kPa (absolute pressure), and an operating temperature of more than 150° C.;

(ii) operating conditions involving a hydrogen partial pressure of 5 kPa or less (absolute pressure), a carbon dioxide partial pressure of less than 20 kPa (absolute pressure), and an operating temperature of more than 100° C.;

(iii) the oxygen concentration in a gas phase is less than 7 percent by volume; and (iv) the oxygen concentration in a liquid phase is less than $7 \times 10^{-5}$ g/g.

22 Claims, 5 Drawing Sheets

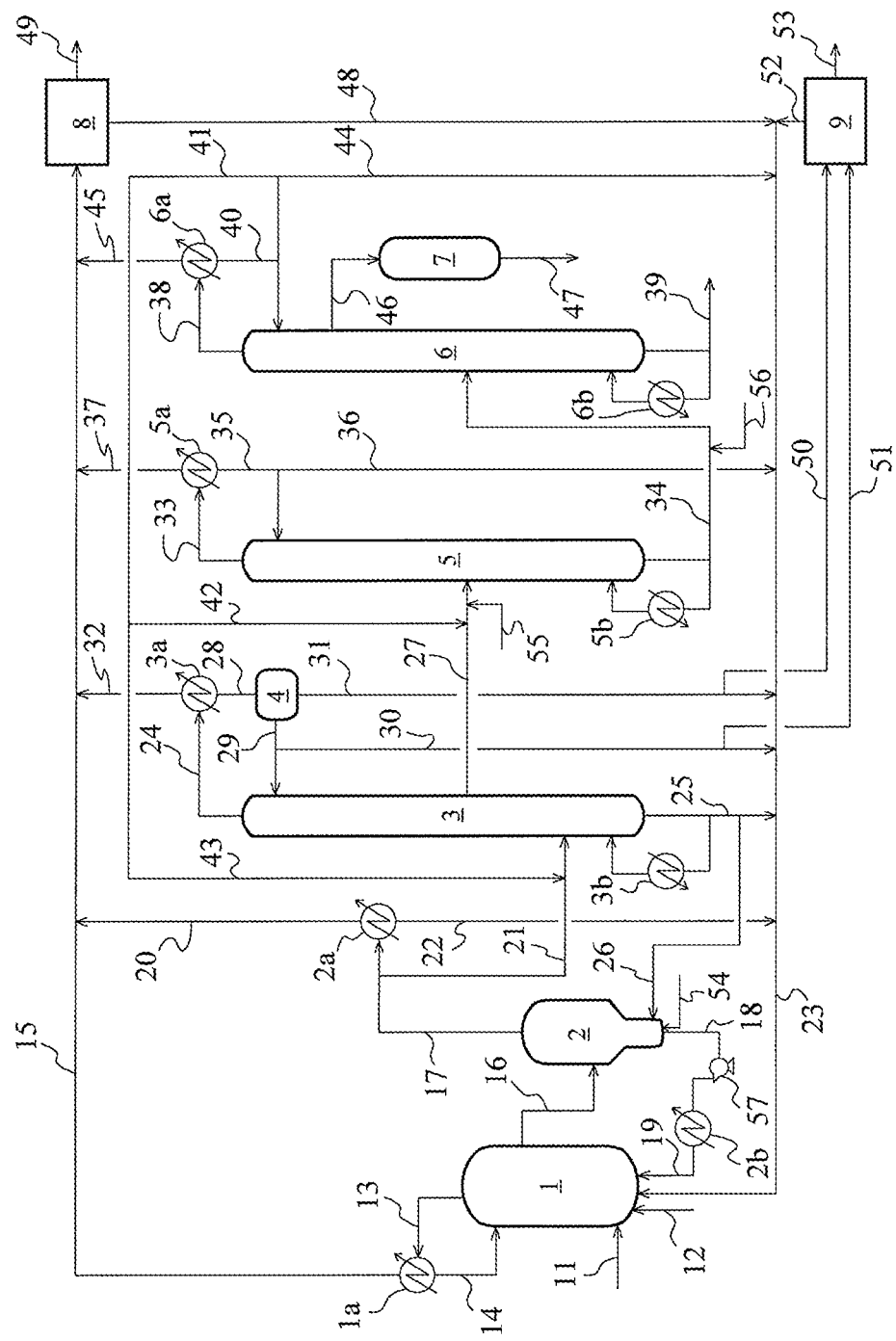
[FIG. 1]

[FIG. 2]
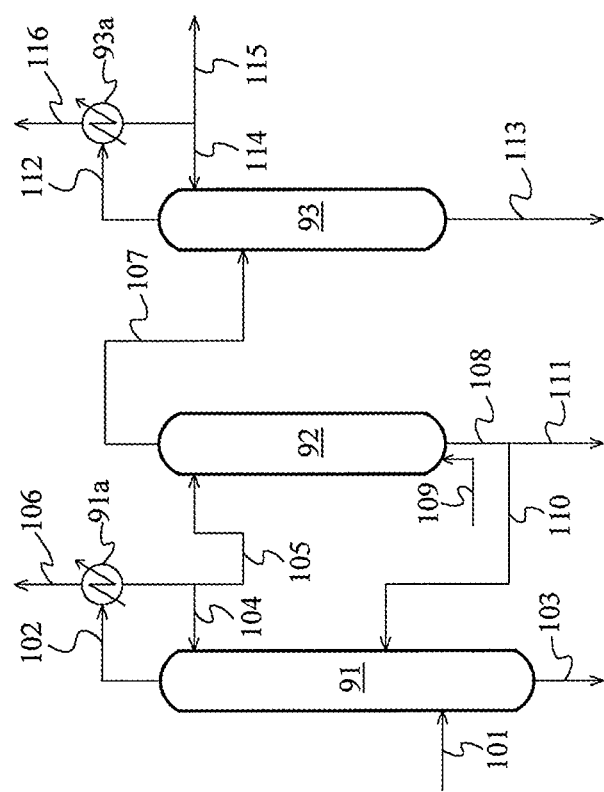

[FIG. 3]
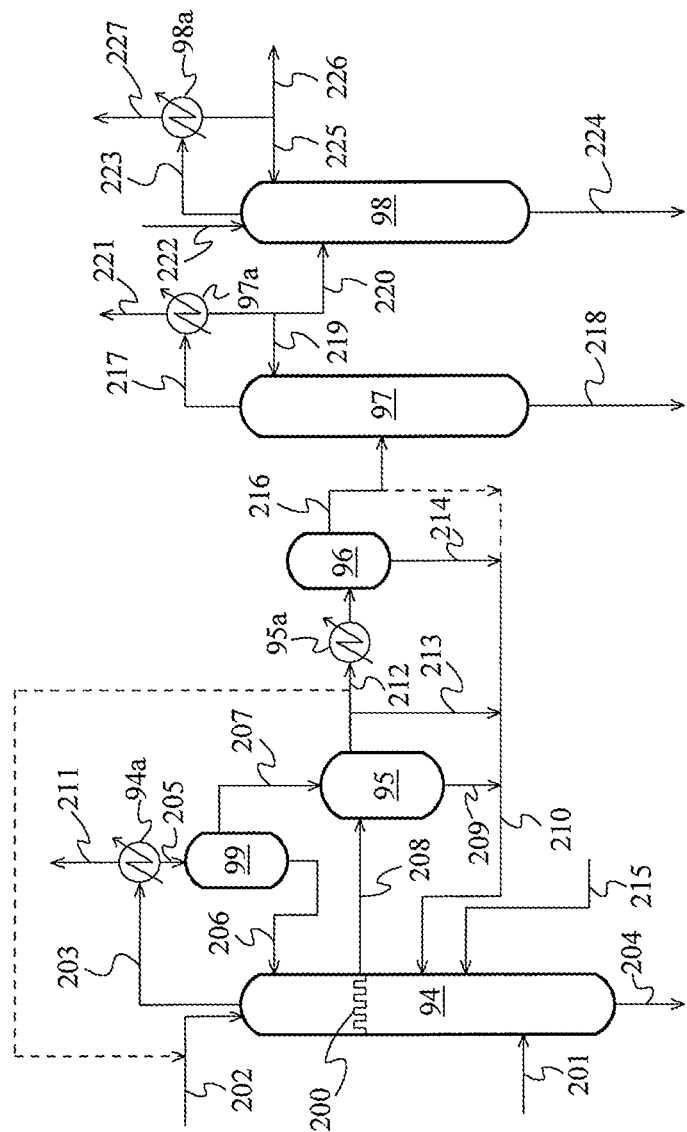

[FIG. 4]
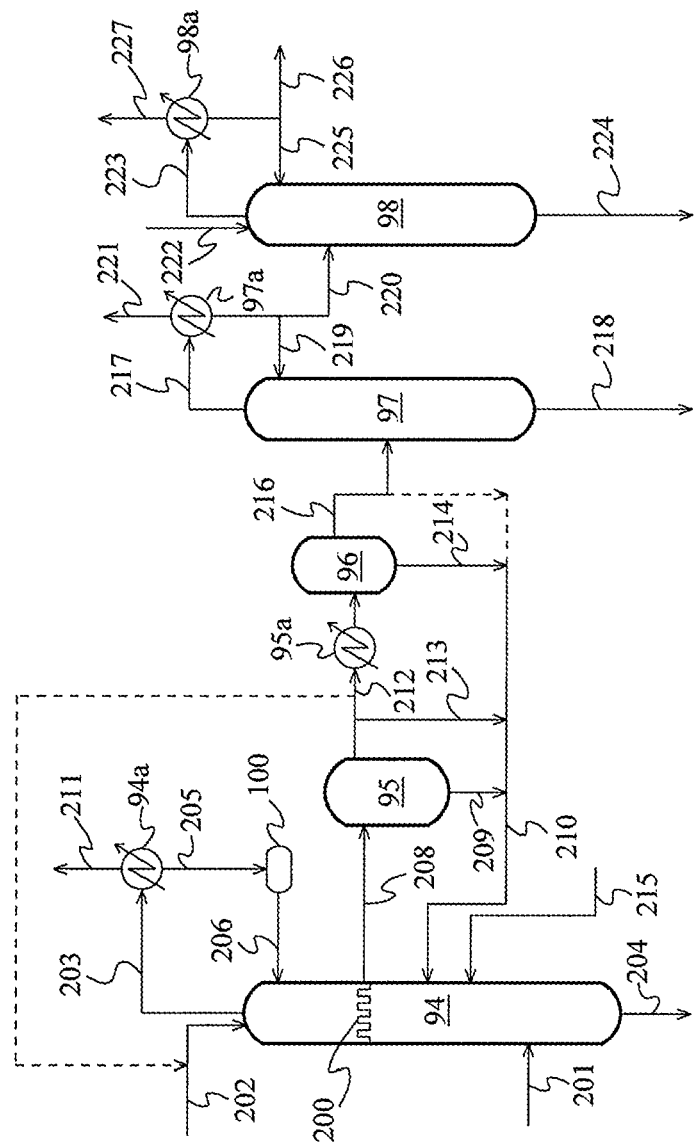

[FIG. 5]
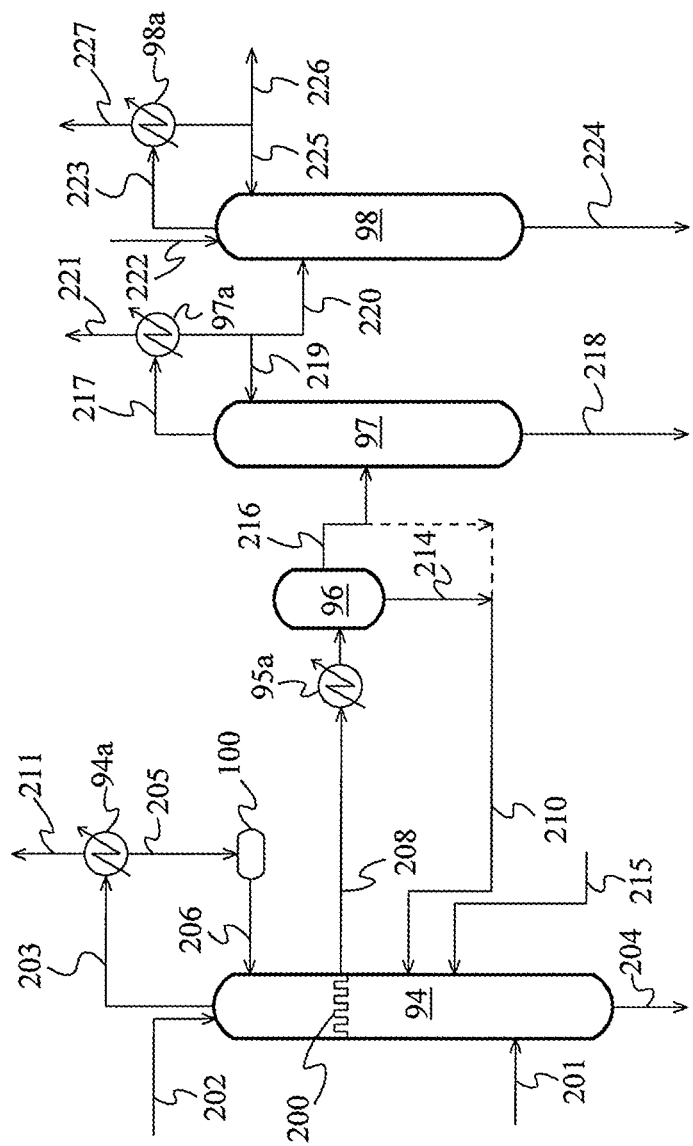

METHOD FOR PRODUCING ACETIC ACID

TECHNICAL FIELD

The present invention relates to methods for producing acetic acid.

BACKGROUND ART

A methanol carbonylation process (methanol-acetic acid process) is known as a process for industrially producing acetic acid. With this process, an acetic acid product is produced typically by allowing methanol to react with carbon monoxide in the presence of a catalyst in a reactor, to form acetic acid in a reaction mixture, evaporating the reaction mixture using an evaporator into a vapor phase, and purifying the vapor phase through a light ends column, and subsequently through a dehydration column to give an acetic acid product. Alternatively, the product from the dehydration column is further fed to a subsequent heavy ends column and, in some cases, a subsequent product column to give an acetic acid product.

In such an acetic acid production process, formic acid is produced as a by-product in the reactor. The minimum amount of formic acid is favorable because the formic acid reduces the purity of an acetic acid product. Patent Literature 1 and 2 each disclose that formic acid is formed through the reaction of carbon monoxide with water; and therefore, the formic acid concentration in acetic acid product can be lowered by controlling a water concentration in a reaction medium to a low level. However, there is the problem that a catalyst tends to become unstable if the water concentration in the reaction medium is decreased.

CITATION LIST

Patent Literature

PTL 1: U.S. Patent Application Publication No. 2008/0293966
PTL 2: U.S. Patent Application Publication No. 2008/0293967

SUMMARY OF INVENTION

Technical Problem

Therefore, an object of the present invention is to provide a method capable of lowering a formic acid concentration in acetic acid product by a simple approach.

Further, another object of the present invention is to provide a method for producing acetic acid capable of effectively preventing local corrosion of acetic acid production equipment, and a method for producing acetic acid capable of effectively suppressing coloration of acetic acid product.

Solution to Problem

In order to attain the object, the present inventor has conducted diligent studies to discover a mechanism underlying formic acid formation, and consequently gained the knowledge that: more than a little formic acid is formed, mainly, in a reactor, an evaporator, and a light ends column where hydrogen and carbon dioxide are present; at a higher hydrogen partial pressure and carbon dioxide partial pressure, more formic acid is formed; at a higher temperature, formic acid formation is suppressed; the presence of equilibrium reaction of $H_2 + CO_2 \leftrightarrow HCOOH$ is predicted from these; etc. Further, the present inventor also gained the knowledge that oxygen is mixed in the process stream due to various factors, such as the components to be introduced into the process from the outside, formaldehyde is formed in the presence of methanol and oxygen, and formic acid is formed in the presence of the formed formaldehyde and oxygen. Accordingly, the present inventor conducted further studies and found that: for suppressing formic acid formation, it is desirable to maintain a low hydrogen partial pressure, a low carbon dioxide partial pressure, a high temperature, and a low oxygen partial pressure; formic acid can be decomposed by recycling a process liquid containing the formic acid to a reactor, an evaporator, or a distillation column and maintaining a low hydrogen partial pressure, a low carbon dioxide partial pressure, and a high temperature; because formic acid has a lower boiling point than that of acetic acid and is therefore concentrated at the column top of each distillation column, an overhead liquid of the distillation column is recycled to the reaction system or a distillation column positioned upstream from the distillation column so that formic acid can be decomposed; etc. The present invention is based on these findings and has been completed through further studies.

Specifically, the present invention provides a method for producing acetic acid, comprising at least one step selected from a step that satisfies the following operating condition (i) and a step that satisfies the following operating condition (ii) in an acetic acid production process, and controlling an oxygen concentration in an embodiment satisfying at least one selected from the following (iii) and (iv) for one or more processes:

(i) operating conditions involving a hydrogen partial pressure of less than 500 kPa (absolute pressure), a carbon dioxide partial pressure of less than 70 kPa (absolute pressure), and an operating temperature of more than 150° C.;

(ii) operating conditions involving a hydrogen partial pressure of 5 kPa or less (absolute pressure), a carbon dioxide partial pressure of less than 20 kPa (absolute pressure), and an operating temperature of more than 100° C.;

(iii) the oxygen concentration in a gas phase is less than 7 percent by volume; and (iv) the oxygen concentration in a liquid phase is less than $7 \times 10^{-5}$ g/g.

The operating condition (ii) may involve a hydrogen partial pressure of 1 kPa or less (absolute pressure) and a carbon dioxide partial pressure of less than 2 kPa (absolute pressure).

The method for producing acetic acid according to the present invention may have a reaction step that satisfies the operating condition (i). In this case, a liquid reaction mixture in the reaction step may have an acetic acid concentration of 30 percent by mass or more and a formic acid concentration of 102 ppm by mass or less. Also, the liquid reaction mixture in the reaction step may have an acetic acid concentration of 50 to 90 percent by mass, a metal catalyst concentration (in terms of metal) of 200 to 10000 ppm by mass, a methyl iodide concentration of 1 to 20 percent by mass, an ionic iodide concentration of 1 to 25 percent by mass, a water concentration of 0.1 to 15 percent by mass, a methyl acetate concentration of 0.1 to 30 percent by mass, and a formic acid concentration of 102 ppm by mass or less.

The method for producing acetic acid according to the present invention may have an evaporation step or a distillation step that satisfies the operating condition (ii). A charge liquid to an evaporator in the evaporation step may have an acetic acid concentration of 50 to 90 percent by mass, a metal catalyst concentration (in terms of metal) of 200 to 10000 ppm by mass, a methyl iodide concentration of 1 to 20 percent by mass, an ionic iodide concentration of 1 to 25 percent by mass, a water concentration of 0.1 to 15 percent by mass, a methyl acetate concentration of 0.1 to 30 percent by mass, and a formic acid concentration of 10000 ppm by mass or less. Also, a charge liquid to a distillation column in the distillation step may have an acetic acid concentration of 30 percent by mass or more and a formic acid concentration of 5 ppm by mass or more. Furthermore, a charge liquid to a distillation column in the distillation step may have an acetic acid concentration of 40 to 85 percent by mass, a methyl iodide concentration of 2 to 50 percent by mass, a water concentration of 0.2 to 20 percent by mass, a methyl acetate concentration of 0.2 to 50 percent by mass, and a formic acid concentration of 5 to 10000 ppm by mass. Moreover, a charge liquid to a distillation column in the distillation step may have an acetic acid concentration of 80 to 99.9 percent by mass, a methyl iodide concentration of 0.01 to 16 percent by mass, a water concentration of 0.05 to 13 percent by mass, a methyl acetate concentration of 0.01 to 16 percent by mass, and a formic acid concentration of 5 to 10000 ppm by mass. Also, a charge liquid to a distillation column in the distillation step may have an acetic acid concentration of 99.1 to 99.999 percent by mass and a formic acid concentration of 5 to 9000 ppm by mass.

In the above (iii), it is preferred that a ratio of oxygen to carbon monoxide in the gas phase be 2 percent by volume or less. Further, in the above (iv), it is preferred that the ratio of oxygen to carbon monoxide in the liquid phase be 2 percent by volume or less.

In the above (iii) and/or (iv), it is preferred that at least one component selected from the group consisting of an oxygen-containing gas, an oxygen-containing compound, and an oxygen generating agent be introduced to be the oxygen concentration in the gas phase in the above (iii) of 1 ppt by volume or more and/or the oxygen concentration in the liquid phase in the above (iv) of $0.1 \times 10^{-9}$ g/g or more.

In the above (iii) and/or (iv), it is preferred the oxygen concentration be a concentration of 0.25 mol or less with respect to a total of 1 mol of hydrogen iodide and methyl iodide.

In the method for producing acetic acid according to the present invention, the gas phase in the above (iii) and/or the liquid phase in the above (iv) may be a gas phase and/or a liquid phase in the reaction step, the evaporation step, or the distillation step.

In the method for producing acetic acid according to the present invention, the acetic acid production process may have a carbonylation step of reacting methanol with carbon monoxide to produce acetic acid, an evaporation step of separating the reaction mixture obtained in the carbonylation step into a vapor stream and a residue stream, and a light ends-removing step of separating the vapor stream into an overhead stream rich in light ends and a first acetic acid stream rich in acetic acid by subjecting the vapor stream to distillation, or in addition to these steps, further comprises at least one step from among the following (a) to (d):

(a) a dehydration step of separating the first acetic acid stream by distillation into an overhead stream rich in water and a second acetic acid stream more enriched with acetic acid than the first acetic acid stream;

(b) a heavy ends-removing step of separating the first or the second acetic acid stream by distillation into a bottoms stream rich in heavy ends and a third acetic acid stream more enriched with acetic acid than the acetic acid stream before being subjected to distillation;

(c) an adsorptive removing step of treating the first, second, or third acetic acid stream with an ion exchange resin to obtain a fourth acetic acid stream; and (d) a product step of distilling the first, second, third, or fourth acetic acid stream to obtain a fifth acetic acid stream more enriched with acetic acid than the acetic acid streams before being subjected to distillation.

In this case, the carbonylation step may satisfy the operating condition (i). Further, at least one step selected from the evaporation step, the light ends-removing step, the dehydration step, the heavy ends-removing step, and the product step may satisfy the operating condition (ii).

In the method for producing acetic acid according to the present invention, it is preferred that a retention time in the step that satisfies the operating condition (i) or the step that satisfies the operating condition (ii) be 1 minute or more.

In the method for producing acetic acid according to the present invention, it is preferred that the gas phase and/or the liquid phase in at least one step selected from the carbonylation step, the evaporation step, the light ends-removing step, the dehydration step, the heavy ends-removing step, and the product step be a gas phase in the above (iii) and/or a liquid phase in the above (iv).

In the method for producing acetic acid according to the present invention, a process liquid having a formic acid concentration of 10 ppm by mass or more may be recycled to a step that satisfies operating conditions involving a hydrogen partial pressure of less than 500 kPa (absolute pressure), a carbon dioxide partial pressure of less than 70 kPa (absolute pressure), and an operating temperature of more than 100° C.

In the method for producing acetic acid according to the present invention, the acetic acid production process may have at least one distillation step, and an overhead liquid of a distillation column in the at least one distillation step may be recycled to the step that satisfies the operating condition (i) and/or the step that satisfies the operating condition (ii). In this case, the step to which the overhead liquid of a distillation column is recycled may be the reaction step and/or the evaporation step or a distillation step positioned upstream from the distillation step associated with the distillation column.

Advantageous Effects of Invention

According to the present invention, formic acid formation can be suppressed, or formed formic acid can be efficiently decomposed, because of having a step that satisfies particular operating conditions. Therefore, a formic acid concentration in acetic acid product can be simply lowered.

BRIEF DESCRIPTION OF DRAWINGS

FIG. 1 is a flow chart illustrating acetic acid production according to an embodiment of the present invention;

FIG. 2 is a schematic flow chart illustrating an acetaldehyde separation and removal system according to an embodiment;

FIG. 3 is a schematic flow chart illustrating an acetaldehyde separation and removal system according to another embodiment;

FIG. 4 is a schematic flow chart illustrating an acetaldehyde separation and removal system according to yet another embodiment; and FIG. 5 is a schematic flow chart illustrating an acetaldehyde separation and removal system according to still another embodiment.

DESCRIPTION OF EMBODIMENTS

The method for producing acetic acid according to the present invention comprises at least one step selected from a step that satisfies the following operating condition (i) and a step that satisfies the following operating condition (ii) in an acetic acid production process, and controlling an oxygen concentration in an embodiment satisfying at least one selected from the following (iii) and (iv) for one or more processes:

(i) operating conditions involving a hydrogen partial pressure of less than 500 kPa (absolute pressure), a carbon dioxide partial pressure of less than 70 kPa (absolute pressure), and an operating temperature of more than 150° C.;

(ii) operating conditions involving a hydrogen partial pressure of 5 kPa or less (absolute pressure), a carbon dioxide partial pressure of less than 20 kPa (absolute pressure), and an operating temperature of more than 100° C.;

(iii) the oxygen concentration in a gas phase is less than 7 percent by volume; and (iv) the oxygen concentration in a liquid phase is less than $7 \times 10^{-5}$ g/g.

The operating condition (i) in the step satisfying the above-mentioned operating condition (i) are operating conditions during continuous operation in the method for producing acetic acid by continuous operation. For example, in a case that the process conditions may fluctuate, the operating conditions are operating conditions in a stable condition that hardly change. The same applies to the operating conditions satisfying the above (ii), the operating conditions satisfying the above (iii), and the operating conditions satisfying the above (iv).

In the step that satisfies the operating condition (i) or operating condition (ii), formic acid formation is effectively suppressed, while formic acid in a feeding liquid for the step is efficiently decomposed. This is presumably because equilibrium reaction of $H_2+CO_2 \leftrightarrow HCOOH$ exists, and this equilibrium is shifted to the left side under the operating conditions described above. The step satisfying the above operating conditions may be any of the reaction step, the various steps included in the separation step (to be described later) (e.g., evaporation step, distillation step, etc.), or a step not included in the separation step. In the present specification, "distillation step" means a step for distilling acetic acid, for example, a light ends-removing step, a dehydration step, a light ends-water-removing step, a heavy ends-removing step, a product step, and the like (to be described later).

In the present specification, the "hydrogen partial pressure" and the "carbon dioxide partial pressure" mean partial pressures of these components in a gas phase portion in an apparatus or equipment (a reactor, an evaporator, a distillation column, etc.) for use in the step. In the distillation column, the partial pressures in a gas phase portion of at least one plate (e.g., a bottom plate, a feeding plate, or an uppermost plate) can fall within the range described above. It is preferred that the partial pressures in a gas phase portion of each plate from the feeding plate to the uppermost plate should fall within the range described above. It is more preferred that the partial pressures in a gas phase portion of each plate from the bottom plate to the uppermost plate should fall within the range described above. The "operating temperature" means the temperature of a liquid phase portion or a gas phase portion in an apparatus or equipment (a reactor, an evaporator, a distillation column, etc.) for use in the step. In the distillation column, the temperature of a liquid phase portion or a gas phase portion of at least one plate (e.g., a bottom plate, a feeding plate, or an uppermost plate) can fall within the range described above. It is preferred that the temperature of a liquid phase portion or a gas phase portion of each plate from the feeding plate to the uppermost plate should fall within the range described above. It is more preferred that the temperature of a liquid phase portion or a gas phase portion of each plate from the bottom plate to the uppermost plate should fall within the range described above.

In the operating condition (i), the hydrogen partial pressure (absolute pressure) can be less than 500 kPa and is preferably 400 kPa or less, more preferably 300 kPa or less, further preferably 200 kPa or less, and particularly preferably 150 kPa or less. Although the lower limit of the hydrogen partial pressure (absolute pressure) is 0 kPa, from the perspective of increasing catalytic activity with hydrogen, the hydrogen partial pressure (absolute pressure) may be more than 1 kPa (or more than 5 kPa). The carbon dioxide partial pressure (absolute pressure) can be less than 70 kPa and is preferably 60 kPa or less, more preferably 50 kPa or less further preferably 40 kPa or less, and particularly preferably 30 kPa or less. The lower limit of the carbon dioxide partial pressure (absolute pressure) is 0 kPa. Carbon dioxide and hydrogen are present in the carbon monoxide used as a raw material for the methanol-carbonylation reaction, and are also produced in the reactor by the water gas shift reaction, and hence it is economically disadvantageous to use a raw material carbon monoxide in which the carbon dioxide and the hydrogen partial pressure have been overly reduced. Therefore, the lower limit of the carbon dioxide partial pressure (absolute value) may be 2 kPa (or 20 kPa). The operating temperature can be a temperature of more than 150° C., and is for example more than 160° C., preferably more than 175° C., more preferably 173° C. or more, further preferably 181° C. or more, and particularly preferably 184° C. or more. The upper limit of the operating temperature is, for example, 250° C., preferably 230° C., and more preferably 200° C.

In the operating condition (ii), the hydrogen partial pressure (absolute pressure) can be 5 kPa or less and is preferably 4 kPa or less, more preferably 3 kPa or less, further preferably 2 kPa or less, and particularly preferably 1 kPa or less. The lower limit of the hydrogen partial pressure (absolute pressure) is 0 kPa, but because it is economically disadvantageous to completely remove the hydrogen that may become mixed in the reaction mixture, the lower limit may be set to be more than 0.0001 kPa. The carbon dioxide partial pressure (absolute pressure) can be less than 20 kPa, and is preferably 18 kPa or less, more preferably 16 kPa or less, further preferably 14 kPa or less, and particularly preferably 12 kPa or less. The lower limit of the carbon dioxide partial pressure (absolute pressure) is 0 kPa, but because it is economically disadvantageous to completely remove the carbon dioxide that may become mixed in the reaction mixture, the lower limit may be set to be more than 0.0001 kPa. The operating temperature can be a temperature of more than 100° C., and is preferably 102° C. or more, more preferably 104° C. or more, even more preferably 106° C. or more, and particularly preferably 112° C. or more. The upper limit of the operating temperature is, for example, 250° C., preferably 200° C., more preferably 175° C.

In the operating condition (ii), the hydrogen partial pressure (absolute pressure) may be 1 kPa or less, and the carbon dioxide partial pressure (absolute pressure) may be less than 2 kPa. In this case, the upper limit of the hydrogen partial pressure (absolute pressure) is preferably 0.9 kPa, more preferably 0.8 kPa. The lower limit of the hydrogen partial pressure (absolute pressure) is 0 kPa, but the lower limit may be set to be more than 0.0001 kPa. The upper limit of the carbon dioxide partial pressure (absolute pressure) is preferably 1.8 kPa, more preferably 1.5 kPa, further preferably 1.0 kPa, and particularly preferably 0.5 kPa. The lower limit of the carbon dioxide partial pressure (absolute pressure) is 0 kPa, but the lower limit may be set to be more than 0.0001 kPa.

Examples of the step that satisfies the operating condition (i) include a reaction step. In this case, it is preferred that a liquid reaction mixture in the reaction step should have an acetic acid concentration of 30 percent by mass or more (e.g., 30 to 90 percent by mass) and a formic acid concentration of 102 ppm by mass or less (0 to 102 ppm by mass). Further preferably, the liquid reaction mixture in the reaction step has an acetic acid concentration of 50 to 90 percent by mass (e.g., 60 to 80 percent by mass), a metal catalyst concentration (in terms of metal) of 200 to 10000 ppm by mass (e.g., 300 to 5000 ppm by mass, preferably 400 to 2000 ppm by mass), a methyl iodide concentration of 1 to 20 percent by mass (e.g., 5 to 15 percent by mass), an ionic iodide concentration of 1 to 25 percent by mass (e.g., 5 to 20 percent by mass), a water concentration of 0.1 to 15 percent by mass (e.g., 0.8 to 10 percent by mass), a methyl acetate concentration of 0.1 to 30 percent by mass (e.g., 1 to 10 percent by mass), and a formic acid concentration of 102 ppm by mass or less (e.g., 0 to 85 ppm by mass).

Examples of the step that satisfies the operating condition (ii) include an evaporation step and a distillation step. The distillation step may be a step that is included in the separation step described later, or may a step that is not included in the separation step described later. In the evaporation step that satisfies the operating condition (ii), a charge liquid to an evaporator may have an acetic acid concentration of 50 to 90 percent by mass (e.g., 60 to 80 percent by mass), a metal catalyst concentration (in terms of metal) of 200 to 10000 ppm by mass (e.g., 300 to 5000 ppm by mass, preferably 400 to 2000 ppm by mass), a methyl iodide concentration of 1 to 20 percent by mass (e.g., 5 to 15 percent by mass), an ionic iodide concentration of 1 to 25 percent by mass (e.g., 5 to 20 percent by mass), a water concentration of 0.1 to 15 percent by mass (e.g., 0.8 to 10 percent by mass), a methyl acetate concentration of 0.1 to 30 percent by mass (e.g., 1 to 10 percent by mass), and a formic acid concentration of 10000 ppm by mass or less (e.g., 0 to 1000 ppm by mass, preferably 10 to 500 ppm by mass, more preferably 15 to 200 ppm by mass, further preferably 20 to 100 ppm by mass).

In the distillation step that satisfies the operating condition (ii), a charge liquid to a distillation column in which the distillation step is carried out may have an acetic acid concentration of 30 percent by mass or more (e.g., 30 to 99.999 percent by mass) and a formic acid concentration of 1 ppm by mass or more (e.g., 5 ppm by mass or more, preferably 5 to 10000 ppm by mass). Also, in the distillation step, a charge liquid to a distillation column may have an acetic acid concentration of 40 to 85 percent by mass (e.g., 50 to 75 percent by mass), a methyl iodide concentration of 2 to 50 percent by mass (e.g., 5 to 30 percent by mass), a water concentration of 0.2 to 20 percent by mass (e.g., 1 to 15 percent by mass), a methyl acetate concentration of 0.2 to 50 percent by mass (e.g., 2 to 30 percent by mass), and a formic acid concentration of 1 ppm by mass or more (e.g., 5 to 10000 ppm by mass, preferably 10 to 1000 ppm by mass, more preferably 10 to 500 ppm by mass, further preferably 15 to 200 ppm by mass, particularly preferably 20 to 100 ppm by mass). Furthermore, in the distillation step, a charge liquid to a distillation column in which the distillation step is carried out may have an acetic acid concentration of 80 to 99.9 percent by mass (e.g., 90 to 99.9 percent by mass, preferably 93 to 99 percent by mass), a methyl iodide concentration of 0.01 to 16 percent by mass (e.g., 0.1 to 8 percent by mass, preferably 0.2 to 5 percent by mass), a water concentration of 0.05 to 18 percent by mass (e.g., 0.1 to 8 percent by mass, preferably 0.2 to 5 percent by mass), a methyl acetate concentration of 0.01 to 16 percent by mass (e.g., 0.1 to 8 percent by mass, preferably 0.2 to 5 percent by mass), and a formic acid concentration of 1 percent by mass or more (e.g., 5 to 10000 ppm by mass, preferably for example 10 to 1000 ppm by mass, more preferably 10 to 500 ppm by mass, further preferably 15 to 200 ppm by mass, particularly preferably 20 to 100 ppm by mass). Moreover, in the distillation step, a charge liquid to a distillation column in which the distillation step is carried out may have an acetic acid concentration of 99.1 to 99.999 percent by mass and a formic acid concentration of 1 percent by mass or more (e.g., 5 to 9000 ppm by mass, preferably 10 to 1000 ppm by mass, more preferably 10 to 500 ppm by mass, further preferably 15 to 200 ppm by mass, particularly preferably 20 to 100 ppm by mass).

Further, by controlling the oxygen concentration in one or more processes according to an embodiment of the above (iii) or (iv), formation of formic acid is effectively suppressed. This is presumably because when methanol derived from a methanol source (e.g., methanol, methyl acetate, or dimethyl ether) or methanol in the process reacts with oxygen, formaldehyde is formed by an oxidation reaction ($CH_3OH + 1/2 O_2 \rightarrow HCHO + H_2O$), and if the formed formaldehyde further reacts with oxygen, an oxidation reaction ($HCHO + 1/2 O_2 \rightarrow HCOOH$) would be expected to proceed to form formic acid. The process of controlling the oxygen concentration may be any of the reaction step, the various steps included in the separation step (to be described later) (e.g., evaporation step, distillation step, etc.), or a step not included in the separation step.

In the above (iii) and (iv), the gas phase or the liquid phase controlling the oxygen concentration means a gas phase or a liquid phase in at least one process among all the gas phases and liquid phases in the acetic acid production process. For example, the gas phase may be a gas phase in at least one of any of the apparatus and equipment in the acetic acid production process, or may be an off-gas to be supplied to the scrubber system. The gas phase may even be a gas phase in at least one of the reactors, evaporators, and distillation columns in the acetic acid production process. Further, the gas phase or the liquid phase may have a concentration in the gas phase portion or the liquid phase portion of at least one plate (e.g., bottom plate, feeding plate, or the uppermost plate) in a distillation column within the range described above. However, it is preferred that the concentration of the gas phase portion or the liquid phase portion of each plate between the feeding plate and the uppermost plate be within the range described above, and more preferred that the concentration of the gas phase portion or the liquid phase portion of each plate between the bottom plate and the uppermost plate be within the range described above.

In the present specification, the term "process" means a step of performing a process unit operation such as reaction, evaporation, distillation, cooling, condensation, separation, storage, absorption, and the like, or an apparatus or piece of equipment for performing such a process unit operation, in the acetic acid production apparatus. For example, examples of the apparatus or equipment include a pipe, a reactor, an evaporator, a distillation column, and the like. Also, "process liquid" means the liquid phase in the process, and "process stream" means the liquid phase or the gas phase in the process.

The oxygen concentration in the gas phase can be measured using a known oxygen concentration meter, for example, a magnetic pressure type oxygen analyzer for an explosion proof process (trade name "MPA-51d/p", manufactured by Horiba, Ltd.), a standalone zirconia type oxygen concentration meter (trade names "ZR402G" and "ZR22G", manufactured by Yokogawa Electric Corporation), and a laser type gas analyzer (trade name "SITRANS SL", manufactured by Siemens AG) using near-infrared light.

The oxygen concentration in the liquid phase can be measured using a known oxygen concentration meter (dissolved oxygen sensor), for example, the "DO", "OC", "ODM", and "OBM" models manufactured by DKK-Toa Corporation, the "DO meter" manufactured by Iijima Electronics Industry Co., Ltd., an oxygen concentration meter manufactured by Mettler, which is capable of even measuring the dissolved oxygen concentrations in water and solvents (methanol), and the "OX Model" manufactured by Yokogawa Electric Corporation for measuring oxygen concentration in gas.

The oxygen concentration of a gas phase or a liquid phase whose oxygen concentration is less than the measurement limit value may be measured by utilizing a conventional method (e.g., a method of selectively adsorbing oxygen with an adsorbent, a method of allowing oxygen to selectively permeate a selectively permeable membrane such as an oxygen-enriched membrane, a distillation method of separating into light components and heavy components, an extraction method, etc.) to generate a condensed component enriched in oxygen from the gas phase or the liquid phase, measure the oxygen concentration of that condensed component, and convert the measured value into the oxygen concentration of the gas phase or the liquid phase.

In the present specification, the total amount of the mixture forming each phase of the gas phase and the liquid phase is 100% including impurities. If the mixture forming the gas phase contains a condensable component, even if it is in a gas state under process conditions (temperature and pressure), the composition of the gas phase mixture may not be accurately measured under process conditions as a result of temperature decreasing due to sampling, causing the condensable component to liquefy at ordinary temperature and pressure (25° C., 1 atm≈0.1 MPa). Therefore, the composition of the mixture forming the gas phase is expressed in terms of the volume or mass of the gas phase mixture at a temperature of 25° C. Also, the composition of the mixture (liquid mixture) forming the liquid phase is expressed in terms of mass.

In the acetic acid production process, water is present as a result of water being charged or due to the formation of water by side reactions and the like. For example, water is charged in the reaction process, and an overhead stream rich in light ends from the light ends column (splitter column) is distilled in the acetaldehyde-removing column in the acetaldehyde separation and removal system to produce an acetaldehyde-rich overhead stream. Water is used for the extraction of this acetaldehyde-rich overhead stream (in an extraction column, extractive distillation column, etc.). Further, in the dehydration column, an aqueous solution of an alkali metal hydroxide may be used to remove hydrogen iodide. A trace amount of oxygen is also dissolved in the water in both of the above-mentioned cases, and that oxygen becomes mixed into the process stream using such water.

In addition, in the acetic acid production process by carbonylation, devices such as tanks, hold tanks, pumps, measuring instruments (liquid level gauge, pressure gauge, etc.), and the like are arranged between the reactor and the product column. To prevent liquefaction due to backflow of a process stream (e.g., acetic acid stream) to the measurement instruments, and to prevent carbon monoxide leaking from the stirring shaft of the reactor, the high-pressure seal portions and the like may be purged with nitrogen gas. As a result nitrogen gas is charged into the process from the purging of the instruments with nitrogen gas, and if the seal portion of the stirring shaft is pressure-sealed, a part of the nitrogen gas may leak into the reactor through the seal portion. Such nitrogen gas also contains a trace amount of oxygen.

Further, when oxygen is present in the process, in addition to the above-mentioned formic acid formation reaction proceeding, the oxygen reacts with hydrogen iodide and methyl iodide in the process to release iodine through an oxidation reaction ($2HI+1/2O_2 \rightarrow I_2+H_2O$, $2CH_3I+1/2O_2 \rightarrow CH_3OCH_3+I_2$ etc.). It was also found that if the produced iodine adheres or sticks to the walls of the apparatus, equipment, or pipes, the adhered portion is selectively or locally corroded, causing pitting corrosion and spot corrosion, which form holes. Usually, hydrogen iodide condenses at the column top of the light ends column, dehydration column, heavy ends column, and product column when the moisture concentration of the atmosphere is 5 percent by mass or less. On the other hand, it was also found that since iodine has a higher boiling point than hydrogen iodide, for example, iodine is discharged together with a high boiling point fraction of the distillation column (e.g., side cut stream of the light ends column, bottoms stream of the dehydration column, side cut stream of the product column), and that iodine becomes mixed in the acetic acid product, increasing the iodine concentration in the product, or in some cases causing the brownish red to reddish brown coloration peculiar to iodine to occur. When iodine is mixed in acetic acid product, it inhibits catalytic activity during production of acetic acid derivatives such as vinyl acetate. Therefore, it is generally necessary to manage the iodine concentration in the acetic acid product to an extremely low concentration of 10 ppb by mass or less. Further, as described above, methanol or an alkali metal hydroxide (potassium hydroxide etc.) may be added to a piece of equipment such as a dehydration column to remove a trace amount of hydrogen iodide as methyl iodide or alkali iodide (potassium iodide etc.). Even in such a method, when iodine is generated from hydrogen iodide and/or methyl iodide, the iodine cannot be removed. Although the concentration of hydrogen iodide decreases in the processes downstream of the equipment such as the dehydration column, hydrogen iodide is produced by the reverse reaction when a process stream mixed with iodine is exposed to a reducing atmosphere. Therefore, if the walls of the apparatus, equipment, or pipes are made of a metal having low corrosion resistance (e.g., low-grade material SUS, Hastelloy C material, etc.), rather than local corrosion by iodine, uniform corrosion by hydrogen iodide may occur.

Since the carbonylation process of methanol (particularly the reaction system) is usually a pressurized system, the oxygen concentration in each process stream in the acetic acid production apparatus can be adjusted by controlling the oxygen concentrations of the raw materials and of each charging line. For example, the oxygen concentration in carbon monoxide can be controlled by appropriately operating the carbon monoxide production process, for example, by controlling the charged amount of oxygen and/or the charged amount of steam relative to the carbon monoxide raw material (coal, natural gas, heavy oil, asphalt, etc.) to completely partially oxidize the carbon monoxide raw material with oxygen. Alternatively, the oxygen concentration in purified carbon monoxide may be measured, and a determination regarding whether to use the carbon monoxide may be made based on the measured value. Still further, the oxygen concentration in the carbon monoxide may be controlled by providing feedback control on the carbon monoxide production process based on the measured value, or the oxygen concentration in the carbon monoxide may be controlled by introducing an inert gas based on the measured value.

For methanol as well, the dissolved oxygen concentration may be measured, and a determination regarding whether to use the methanol may be made based on the measured value, or the dissolved oxygen concentration may be controlled by heating or the like based on the measured value. Further, for the water, aqueous solutions (alkaline aqueous solution (aqueous alkali metal hydroxide solution), sodium hypophosphite aqueous solution, etc.) to be charged into the process (reaction system etc.) as well, the dissolved oxygen concentration may be measured, and a determination regarding whether to use those raw materials may be made based on the measured value. Still further, water or aqueous solutions (e.g., water or aqueous solutions whose oxygen concentration has been reduced by boiling etc.) whose dissolved oxygen concentration has been controlled by heating or the like based on the measured value may also be used.

In addition, it can also be understood that for the gases and liquids to be charged into the processes, the oxygen concentration can be measured in the same manner as described above, and the oxygen concentration of the process streams can be controlled or managed based on the measured value.

Further, the oxygen concentration in the process streams may be controlled by utilizing, for example, a method in which the purge amount of nitrogen gas into the process streams is set to the minimum necessary amount, or a method in which the purge gas is switched to purging with carbon monoxide gas or purging with another inert gas.

In the reduced-pressure processes, the oxygen concentration in the reduced-pressure process streams may be managed by, while maintaining airtightness in order to maintain the operating pressure, controlling to a target pressure while introducing an inert gas, and then starting operation while at the same time measuring the oxygen concentration in the exhaust gas from a vacuum pump.

The oxygen concentrations in the gas phase and the liquid phase may be continuously monitored by detecting the oxygen concentration using an oxygen concentration meter (oxygen sensor) installed at an arbitrary place, such as a distillation column or a pipe in the acetic acid production equipment, and monitoring the measured value, or by sampling from the above-mentioned arbitrary place and periodically analyzing the oxygen concentration. Also, the oxygen concentration may be controlled by comparing the measured value of the oxygen concentration meter with the upper limit reference value (threshold), and when the measured value reaches the threshold, automatically introducing a fluid having a low oxygen concentration into the process stream or switching the fluid to be introduced to a fluid having a low oxygen concentration. Furthermore, when the oxygen concentration has decreased too much (when the threshold serving as the lower limit reference value is reached), an oxygen source may be introduced into the process stream.

In the above (iii), the oxygen concentration in the gas phase may be less than 7 percent by volume, and is preferably 6.5 percent by volume or less (e.g., 6 percent by volume or less), more preferably 5.5 percent by volume or less (e.g., 5 percent by volume or less), further preferably 3 percent by volume or less (e.g., 1 percent by volume or less), particularly preferably 0.5 percent by volume or less (e.g., 0.1 percent by volume or less), and especially preferably 0.01 percent by volume or less (e.g., 0.001 percent by volume or less, or 0.0001 percent by volume or less). The lower limit of the oxygen concentration in the gas phase is 0 percent by volume, but may be 1 ppt by volume or more (e.g., 100 ppt by volume or more), and preferably 1 ppb by volume or more (e.g., 100 ppb by volume or more). When the oxygen concentration is too high, iodine is generated in the process, and the apparatus and equipment may corrode. Also, if the oxygen concentration is too high, formaldehyde and formic acid are formed in the process, and the concentration of formic acid in the acetic acid product may increase. In addition, if a condition in which the oxygen concentration is too low is selected, the raw material carbon monoxide, the raw material methanol, the water to be introduced into the process, and the inert gas (nitrogen etc.) used to purge the instruments such as the liquid level gauges and pressure gauges need to have an extremely low concentration of oxygen or dissolved oxygen, which is economically disadvantageous.

In the above (iv), the oxygen concentration in the liquid phase may be less than $7 \times 10^{-5}$ g/g, and is preferably $2 \times 10^{-5}$ g/g or less (e.g., $1 \times 10^{-5}$ g/g or less), more preferably $0.5 \times 10^{-5}$ g/g or less (e.g., $0.1 \times 10^{-5}$ g/g or less), further preferably $0.05 \times 10^{-5}$ g/g or less (e.g., $0.01 \times 10^{-5}$ g/g or less), and particularly preferably $0.001 \times 10^{-5}$ g/g or less (e.g., $0.0001 \times 10^{-5}$ g/g or less). The lower limit of the oxygen concentration in the liquid phase is 0 g/g, but may be $0.1 \times 10^{-5}$ g/g or more. It is also noted that for the liquid phases, such as the pressurized process liquid and the high temperature process liquid, the oxygen concentration may not be able to be accurately measured due to sampling difficulties, oxygen vaporization, and the like. In such cases, the oxygen concentration in the liquid phase under a plurality of conditions with varying temperature and/or pressure may be measured, and the oxygen concentration in the liquid phase at the actual process temperature and pressure may be determined as an estimated value (estimated value based on an experiment). Alternatively, the oxygen concentration in the liquid phase may be calculated using Aspen+ (plus) (manufactured by Aspen Technology, Inc.). When the oxygen concentration is too high, iodine is generated in the process, and the apparatus and equipment may corrode. Also, if the oxygen concentration is too high, formaldehyde and formic acid are formed in the process, and the concentration of formic acid in the acetic acid product may increase. In addition, if a conditions in which the oxygen concentration is too low is selected, the raw material carbon monoxide, the raw material methanol, the water to be introduced into the process, and the inert gas (nitrogen etc.) used to purge the instruments such as the liquid level gauges and pressure gauges need to have an extremely low concentration of oxygen or dissolved oxygen, which is economically disadvantageous.

The ratio of oxygen to carbon monoxide in the gas phase in the above (iii) and/or in the liquid phase in the above (iv) is, for example, 2 percent by volume or less, and preferably 1 percent by volume or less.

When controlling the oxygen concentration in the above (iii) and/or (iv), it is preferred that at least one kind selected from the group consisting of an oxygen-containing gas, an oxygen-containing compound, and an oxygen generating agent be introduced, and the oxygen concentration in the gas phase in the above (iii) be 1 ppt by volume or more and/or the oxygen concentration in the liquid phase in the above (iv) be $0.1 \times 10^{-9}$ g/g or more.

It is preferred that the oxygen concentration is as low as possible. However, if the oxygen concentration is too low, the reducing nature of the atmosphere is too strong, which may increase the corrosion rate of the apparatus and equipment in the acetic acid production apparatus, such as the distillation columns and pipes. Therefore, to control the oxygen concentration, at least one oxygen source selected from the group consisting of an oxygen-containing gas, an oxygen-containing compound, and an oxygen generating agent may be introduced into the process to control the oxygen concentration in the process stream.

Examples of the oxygen-containing gas include air and the like. Examples of the oxygen-containing compound include ozone and the like. Examples of the oxygen generating agent include peracetic acid, hydrogen peroxide, and the like. These oxygen sources may be used alone or in combination of two or more.

From the perspective of suppressing the generation of iodine, in the above (iii) and (iv), the oxygen concentration in the process stream relative to a total of 1 mol of hydrogen iodide and methyl iodide may be about, for example, 0.25 mol or less (e.g., 0.2 mol or less), preferably 0.1 mol or less (e.g., 0.05 mol or less), more preferably 0.01 mol or less (e.g., $1 \times 10^{-3}$ mol or less), and particularly preferably $1 \times 10^{-4}$ mol or less (e.g., $1 \times 10^{-5}$ mol or less), and may even be $1 \times 10^{-6}$ or less (e.g., $1 \times 10^{-7}$ mol or less).

The ratio of oxygen to carbon monoxide ($O_2$/CO) in the process stream is, for example, 7 percent by volume or less (e.g., 5 percent by volume or less), preferably 2 percent by volume or less (e.g., 1 percent by volume or less), more preferably 0.5 percent by volume or less (e.g., 0.1 percent by volume or less), further preferably 0.01 percent by volume or less (e.g., 0.001 percent by volume or less), and particularly preferably 0.0001 percent by volume or less (e.g., 0.00001 percent by volume or less).

Regarding the above (iv), the oxygen concentration in the liquid phase is often low, and the ratio of oxygen to carbon monoxide ($O_2$/CO) may vary greatly. The mass ratio of oxygen to 100 parts by mass of carbon monoxide in the liquid phase ($O_2$/CO) may be, for example, 1000 parts by mass or less (10 times or less) (e.g., 500 parts by mass or less), 250 parts by mass or less (e.g., 100 parts by mass or less), 75 parts by mass or less (e.g., 50 parts by mass or less), 20 parts by mass or less (e.g., 10 parts by mass or less), 5 parts by mass or less (e.g., 1 part by mass or less), 0.1 parts by mass or less (e.g., 0.01 parts by mass or less), 0.001 parts by mass or less (e.g., 0.0001 parts by mass or less), or 0.00005 parts by mass or less (e.g., 0.00001 parts by mass or less).

In the above (iii) and (iv), in order to suppress by-products of iodine or formic acid, it is preferred that the gas phase or liquid phase in the process include at least one kind selected from methyl iodide, hydrogen iodide and formic acid. In addition, the process stream (e.g., process gas phase) may include, depending on the process, at least one kind selected from the group consisting of acetic acid, methyl acetate, methanol, water, acetaldehyde, a by-product derived from the acetaldehyde, and dialkyl ether. The by-product may include at least one kind selected from the group consisting of alkyl iodides having 2 or more carbon atoms, alkanals having 4 or more carbon atoms, alkane carboxylic acids having 3 or more carbon atoms, alkanes, and ketones, and the dialkyl ether may include at least dimethyl ether.

Examples of the gas phase in the above (iii) include the gas phase in the reaction step, the evaporation step, or the distillation step. Further, examples of the liquid phase in the above (iv) include the liquid phase in the reaction step, the evaporation step, or the distillation step.

By controlling the oxygen concentration in the acetic acid production process as defined in the above (iii) and/or (iv), useful process conditions can be provided that enable the production of iodine and/or formic acid as by-products to be suppressed, and problems such as local corrosion by iodine, an increase in the total iodine concentration and/or formic acid concentration in the acetic acid product, and coloration of the acetic acid product to be solved. In addition, controlling the oxygen concentration as defined in the above (iii) and/or (iv) is very effective in terms of managing the iodine concentration in the acetic acid product to 10 ppb by mass or less and the formic acid concentration to 50 ppm by mass or less, which are very low concentrations. Further, it is known that high-grade corrosion resistant metals such as zirconium exhibit complete corrosion resistance over a wide range of conditions including reducing conditions and oxidizing conditions. However, even such high-grade corrosion resistant metals may be corroded under strongly oxidizing conditions. Therefore, depending on the material selection of the apparatus and equipment, corrosion may occur depending on the oxygen concentration even though the selected material exhibits corrosion resistance up to fairly high oxygen concentrations. With the oxygen concentration control described above, such corrosion can also be suppressed.

In the method for manufacturing acetic acid of the present invention, the process for producing acetic acid may include a carbonylation step of reacting methanol and carbon monoxide to produce acetic acid, and a separation step of separating the reaction mixture obtained in the carbonylation step using one or more evaporators and/or distillation columns into a stream containing a metal catalyst, an acetic acid stream rich in acetic acid, and a stream more enriched with light ends than the acetic acid stream. The separation step preferably comprises, for example, an evaporation step of separating the reaction mixture obtained in the carbonylation step into a vapor stream and a residue stream in an evaporator, and a light ends-removing step of subjecting the vapor stream to distillation to separate the vapor stream into an overhead stream rich in light ends and a first acetic acid stream rich in acetic acid.

Further, in addition to these steps, the method for manufacturing acetic acid of the present invention may further comprise at least one step from among the following (a) to (d). When the method comprises the following step (a), this step (a) is included in the above-mentioned separation step.

(a) a dehydration step of separating the first acetic acid stream by distillation into an overhead stream rich in water and a second acetic acid stream more enriched with acetic acid than the first acetic acid stream;

(b) a heavy ends-removing step of separating the first or the second acetic acid stream by distillation into a bottoms stream rich in heavy ends and a third acetic acid stream more enriched with acetic acid than the acetic acid stream before being subjected to distillation;

(c) an adsorptive removing step of treating the first, second, or third acetic acid stream with an ion exchange resin to obtain a fourth acetic acid stream; and (d) a product step of distilling the first, second, third, or fourth acetic acid stream to obtain a fifth acetic acid stream more enriched with acetic acid than the acetic acid streams before being subjected to distillation.

The separation step may comprise, in place of the evaporation step and the light ends-removing step, a step (evaporative light ends-removing step) of separating the reaction mixture obtained in the carbonylation step into a stream containing the metal catalyst, an overhead stream rich in the light ends, and a first acetic acid stream rich in acetic acid. Further, the separation step may also comprise, instead of the light ends-removing step and the dehydration step, a light ends-removing step (so-called light ends-water-removing step) also having the function of the dehydration step, that is, a step in which the vapor stream is subjected to distillation and separated into an overhead stream rich in light ends and an acetic acid stream dehydrated to a water concentration equivalent to that of the above-mentioned second acetic acid stream. Therefore, the evaporative light ends-removing step may be a step (evaporative light ends-water-removing step) also having the function of the dehydration step. The acetic acid stream rich in acetic acid obtained from the light ends-water-removing step and evaporative light ends-water-removing step corresponds to the second acetic acid stream.

The carbonylation step may satisfy the operating condition (i). Further, at least one step selected from the group consisting of the evaporation step, the light ends-removing step, the evaporative light ends-removing step, the dehydration step, the light ends dehydration step, the evaporative light ends dehydration step, the heavy ends-removing step, and the product step (preferably the light ends-removing step, the evaporative light ends-removing step, the light ends-water-removing step, and the evaporative light ends-water-removing step, more preferably the light ends-removing step and the dehydration step, the evaporation step and the light ends-removing step, the light ends-water-removing step, the evaporative light ends-removing step, or the evaporative light ends-water-removing step, and further preferably the evaporation step and the light ends-removing step and the dehydration step) may satisfy the operating condition (ii). In addition, at least one step selected from the group consisting of the evaporation step, the light ends-removing step, the heavy ends-removing step, and the product step may satisfy the operating condition (ii).

Iodine and/or formic acid tend to be formed more easily in the process stream as the oxygen concentration in the process stream increases. Therefore, it is preferred that the process in which the gas phase or the liquid phase whose oxygen concentration is to be controlled in the above (iii) and (iv) be a process in which hydrogen iodide, methyl iodide, methanol, or formaldehyde tends to be present. Therefore, it is preferred that the gas phase in the above (iii) and/or the liquid phase in the above (iv) respectively be the gas phase and/or liquid phase in one or more steps selected from the group consisting of the reaction step, the various steps included in the separation step (evaporation step, light ends-removing step, dehydration step, evaporative light ends-removing step, light ends-water-removing step, and evaporative light ends-water-removing step), the aqueous phase and the organic phase in the decanter 4 described later, the various steps included in the acetaldehyde separation and removal system (extraction step, distillation step, extractive distillation step, etc.), the high-pressure absorption step, the low-pressure absorption step, and the desorption step. Among those, from the perspective that hydrogen iodide, methyl iodide, methanol, or formaldehyde is more likely to be present, more preferred are the gas phase and/or liquid phase in one or more steps selected from the group consisting of the reaction step (e.g., liquid reaction mixture or gas phase in the reactor), the evaporation step (in particular, volatile phase), the light ends-removing step (in particular, column top of the light ends column), the light ends-water-removing step, the aqueous phase and the organic phase in the decanter A described later, the high-pressure absorption step, and the low-pressure absorption step. It is particularly preferred that the gas phase and/or the liquid phase in one or more steps selected from the group consisting of the reaction step (e.g., liquid reaction mixture or gas phase in the reactor), the evaporation step (in particular, volatile phase), and the light ends-removing step (in particular, column top of light ends column) be the gas phase in the above (iii) and/or the liquid phase in the above (iv).

In addition, in the method for manufacturing acetic acid of the present invention, the gas phase in the above (iii) and/or the liquid phase in the above (iv) may be the gas phase and/or the liquid phase in the reaction step, the evaporation step, or the distillation step. For example, the gas phase and/or the liquid phase in at least one step selected from the group consisting of the reaction step, the evaporation step, the light ends-removing step, the dehydration step, the heavy ends-removing step, and the product step may be the gas phase in the above (iii) and/or the liquid phase in the above (iv).

Further, in the method of the present invention, it is preferred to control the formic acid concentration in at least one process liquid to 500 ppm by mass or less, more preferably 400 ppm by mass or less, even more preferably 300 ppm by mass or less, further preferably 200 ppm by mass or less, and particularly preferably 100 ppm by mass or less, more particularly preferably 50 ppm by mass or less, and even more particularly preferably 30 ppm by mass or less. Also, the formic acid concentration in the liquid phase is 0 ppm by mass or more, and may be for example 0.1 ppm by mass or more (e.g., 1 ppm by mass or more), preferably 3 ppm by mass or more (e.g., 5 ppm by mass or more), more preferably 10 ppm by mass or more, further preferably 15 ppm by mass or more, and particularly preferably 20 ppm by mass or more, and equal to or less than the measurement limit value.

Formic acid tends to be more easily mixed in the acetic acid product as the formic acid concentration in the process liquid increases. Therefore, it is preferred that the process comprising the liquid phase whose formic acid concentration is to be controlled be a process in which methanol or formaldehyde tends to be present. Therefore, it is preferred that the liquid phase be the liquid phase in one or more steps selected from the group consisting of the reaction step, the various steps included in the separation step (e.g., evaporation step, light ends-removing step, evaporative light ends-removing step, light ends-water-removing step, and evaporative light ends-water-removing step), the heavy ends-removing step, the aqueous phase and the organic phase in the decanter 4 described later, the various steps included in the acetaldehyde separation and removal system (extraction step, distillation step, extractive distillation step, etc.), the alkane separation step, the high-pressure absorption step, the low-pressure absorption step, and the desorption step. Among those, from the perspective that methanol or formaldehyde is more likely to be present, more preferred is the liquid phase in one or more steps selected from the group consisting of the reaction step (e.g., liquid reaction mixture), the evaporation step, the light ends-removing step (in particular, column top of the light ends column), the aqueous phase and the organic phase in the decanter 4 described later, the high-pressure absorption step, and the low-pressure absorption step, and particularly preferred is the liquid phase in one or more steps selected from the group consisting of the reaction step (e.g., liquid reaction mixture), the evaporation step, and the light ends-removing step (in particular, column top of light ends column).

The step satisfying the operating condition (i) and/or (ii) may be a process in which the oxygen concentration is controlled so as to satisfy the above (iii) and/or (iv), or may be a process not satisfying the above (iii) and/or (iv). In the above (iii) or (iv), the process comprising the gas phase or the liquid phase whose oxygen concentration is to be controlled may be the same as or different from the process comprising the liquid phase whose formic acid concentration is to be controlled.

Among acetaldehyde and the by-products derived from acetaldehyde, components (aldehydes, alkyl iodides having 2 or more carbon atoms, and the like) that shorten the permanganate time in the permanganate reducing compound test (permanganate time) may be simply referred to as PRCs. Also, unless stated otherwise, an aqueous phase containing acetaldehyde produced by liquid separation is used synonymously with light phase or upper phase, and an organic phase containing methyl iodide is used synonymously with heavy phase, methyl iodide phase, or lower phase. The aqueous phase produced by extraction is used synonymously with extract (extract), and organic phase is used synonymously with raffinate.

Hereinafter, one embodiment of the present invention will be described. FIG. 1 is an acetic acid production flow chart (methanol carbonylation process) according to an embodiment of the present invention. An acetic acid production apparatus associated with this acetic acid production flow has a reactor 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removing step are performed in the reactor 1, the evaporator 2, the distillation column 3, the distillation column 5, the distillation column 6, and the ion exchange resin column 7, respectively. The first distillation step is also referred to as a light ends-removing step, the second distillation step is also referred to as a dehydration step, and the third distillation step is also referred to as a heavy ends-removing step. In the present invention, the steps are not limited to those described above and may exclude, particularly, equipment of the distillation column 5, the distillation column (heavy ends column) 6, the ion exchange resin column 7, the acetaldehyde separation and removal system 9 (acetaldehyde-removing column, etc.). As mentioned later, a product column may be disposed downstream of the ion exchange resin column 7.

The reactor 1 is a unit for performing the reaction step. This reaction step is a step for continuously producing acetic acid through a reaction (methanol carbonylation) represented by the chemical formula (1) given below. In a steady operation state of the acetic acid production apparatus, for example, a reaction mixture under stirring with a stirrer is present in the reactor 1. The reaction mixture contains methanol and carbon monoxide which are raw materials, a metal catalyst a co-catalyst, water, a production target acetic acid and various by-products, and a liquid phase and a gas phase are in equilibrium.

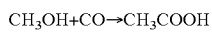

$$CH_3OH + CO \rightarrow CH_3COOH \qquad (1)$$

The raw materials in the reaction mixture are methanol in a liquid state and carbon monoxide in a gaseous state. Methanol is continuously fed at a predetermined flow rate to the reactor 1 from a methanol reservoir (not shown) through the line 11. Carbon monoxide is continuously fed at a predetermined flow rate to the reactor 1 from a carbon monoxide reservoir (not shown) through the line 12. The carbon monoxide is not necessarily required to be pure carbon monoxide and may contain, for example, other gases such as nitrogen, hydrogen, carbon dioxide, oxygen, and helium in a small amount (e.g., 5 percent by mass or less, preferably 1 percent by mass or less). To enhance the catalytic activity, hydrogen may be fed by a line (not shown) merging with the line 12 feeding carbon monoxide, and carbon monoxide may be fed to the reactor 1 as a mixed gas with hydrogen.

The raw materials methanol and carbon monoxide are obtained by purifying syngase (CO, $H_2$, $CO_2$, trace amount $O_2$) generated by partial oxidation of carbon sources (carbon and hydrocarbons) such as fossil fuels (coal, petroleum, etc.), natural gas and the like by oxygen or air, for example, by partial oxidation employing steam methane reforming (SMR), autothermal reforming (ATR), partial oxidation (POX), and the like. Not only partial oxidation using oxygen, but even in SMR the carbon sources and the steam contain oxygen. For this reason, a trace amount of oxygen enters into the process due to for example, the introduction into the reactor of the raw material carbon monoxide and the raw material methanol, and the feeding or addition of methanol into the process to convert hydrogen iodide into methyl iodide for removal Therefore, it is effective to use methanol or carbon monoxide having a low oxygen concentration as a raw material.

For this reason, it is preferred that methanol from which oxygen has been removed in advance be used as the raw material methanol. Also, as for the raw material carbon monoxide, exhaust gas components containing carbon monoxide obtained from a downstream process may be recycled to the reactor. As such carbon monoxide or exhaust gas component, it is preferred that carbon monoxide or exhaust gas from which oxygen has been removed in advance be used.

The metal catalyst in the reaction mixture is for promoting the carbonylation of methanol, and, for example a rhodium catalyst, an iridium catalyst or a cobalt catalyst can be used. For example, a rhodium complex represented by the chemical formula $[Rh(CO)_2I_2]^-$ can be used as the rhodium catalyst. For example, an iridium complex represented by the chemical formula $[Ir(CO)_3I_3]^-$ can be used as the iridium catalyst. A metal complex catalyst is preferred as the metal catalyst. The concentration (in terms of metal) of the catalyst in the reaction mixture is, for example, 200 to 10000 ppm by mass, preferably 300 to 5000 ppm by mass, and more preferably 400 to 2000 ppm by mass, with respect to the whole liquid phase (liquid reaction mixture) of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20 percent by mass (preferably 5 to 15 percent by mass) with respect to the whole liquid phase of the reaction mixture. The ionic iodide is an iodide (particularly, an ionic metal iodide) that generates iodide ions in a reaction solution and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25 percent by mass, preferably 5 to 20 percent by mass, with respect to the whole liquid phase of the reaction mixture. In addition, when an iridium catalyst or the like is used, for example, a ruthenium compound or an osmium compound can be used as the co-catalyst. The amount of these compounds to be used is the total amount, for example 0.1 to 30 moles (in terms of metal), and preferably 0.5 to 15 moles (in terms of metal) with respect to 1 mole of iridium (in terms of metal).

Water in the reaction mixture is a component necessary for generating acetic acid in the reaction mechanism of the methanol carbonylation and is also a component necessary for solubilizing a water-soluble component in the reaction system. The concentration of water in the reaction mixture is, for example, 0.1 to 15 percent by mass, preferably 0.8 to 10 percent by mass, further preferably 1 to 6 percent by mass, and particularly preferably 1.5 to 4 percent by mass, with respect to the whole liquid phase of the reaction mixture. The water concentration is preferably 15 percent by mass or less for pursuing efficient acetic acid production by reducing energy required for the removal of water in the course of purification of acetic acid. In order to control the water concentration, water may be continuously fed at a predetermined flow rate to the reactor 1. It is preferred to remove oxygen from such a catalyst mixture and water in advance by, for example, heating or boiling.

The acetic acid in the reaction mixture includes acetic acid charged in advance into the reactor 1 before operation of the acetic acid production apparatus, and acetic acid generated as a main product of the methanol carbonylation. Such acetic acid can function as a solvent in the reaction system. The concentration of the acetic acid in the reaction mixture is, for example, 50 to 90 percent by mass, preferably 60 to 80 percent by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30 percent by mass, preferably 1 to 10 percent by mass, with respect to the whole liquid phase of the reaction mixture.

Another example of the by-products contained in the reaction mixture includes hydrogen iodide. This hydrogen iodide is inevitably generated under the reaction mechanism of the methanol carbonylation in the case where the catalyst or the co-catalyst as mentioned above is used. The concentration of the hydrogen iodide in the reaction mixture is, for example, 0.01 to 2 percent by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, alkanes, formic acid, propionic acid, and alkyl iodides such as hexyl iodide and decyl iodide. In the present invention, because acetaldehyde can be effectively removed by the acetaldehyde separation and removal system described later, the concentration of acetaldehyde in the reactor can be reduced and the formation of by-products derived from acetaldehyde can be significantly suppressed even in a continuous reaction. The concentration of acetaldehyde in the reaction mixture may be, for example, 1500 ppm by mass or less, 10 to 1000 ppm by mass, 50 to 500 ppm by mass, or 100 to 400 ppm by mass with respect to the entire liquid phase of the reaction mixture.

Examples of the by-products derived from acetaldehyde include: aldehydes such as butyraldehyde, crotonaldehyde, 2-ethylcrotonaldehyde, and 2-ethylbutyraldehyde; ketones such as acetone and methyl ethyl ketone; aldol condensation products thereof; $C_{2-12}$ alkyl iodides such as ethyl iodide, propyl iodide, butyl iodide, pentyl iodide, and hexyl iodide; and the like. Further examples include formic acid and carboxylic acids having 3 or more carbon atoms (linear or branched carboxylic acids such as propionic acid, butanoic acid, pentanoic acid, hexanoic acid, heptanoic acid, octanoic acid, higher fatty acids having 9 or more carbon atoms etc., e.g., $C_{3-12}$ alkane carboxylic acids, etc.); alkyl alcohols (ethanol, butyl alcohol, 2-ethylbutyl alcohol, hexyl alcohol, heptyl alcohol, octyl alcohol, and alkyl alcohols having 9 or more carbon atoms, e.g., $C_{3-12}$ alkyl alcohols, etc.); hydrocarbons having 2 or more carbon atom atoms (e.g., $C_{2-12}$ alkanes); and the like. Furthermore, in the liquid phase system, examples of by-products that are formed include: esters of methanol or these alkyl alcohols with acetic acid or the above-mentioned carboxylic acids (ethyl acetate etc.); dialkyl ethers such as dimethyl ether; and the like. The concentrations of these by-products may be about, across all the processes including the liquid phase system, 0.1 ppb by mass to 100 ppm by mass (e.g., 0.5 ppb by mass to 50 ppm by mass), and preferably 1 ppb by mass to 10 ppm by mass (e.g., 2 ppb by mass to 1 ppm by mass).

The concentration of alkyl iodide having 2 or more carbon atoms such as hexyl iodide is, for example, 0.1 ppb by mass to 1 ppm by mass (e.g., 0.5 to 500 ppb by mass), and preferably 1 to 100 ppb by mass. The concentration of the carboxylic acid having 3 or more carbon atoms is, for example, 0.1 to 500 ppm by mass (e.g., 1 to 500 ppm by mass), and preferably 3 to 100 ppm by mass.

The concentration of dimethyl ether is, for example, 0.5 percent by mass or less (e.g., 0.1 to 1000 ppm by mass), preferably 1 to 500 ppm by mass (e.g., 2 to 300 ppm by mass), and more preferably 3 to 200 ppm by mass (e.g., 5 to 100 ppm by mass).

Furthermore, as the by-product derived from acetaldehyde, a 3-hydroxyalkanal (3-hydroxybutanal or the like) may be produced as a by-product. The concentration of 3-hydroxyalkanal in the reaction mixture is, for example, 100 ppm by mass or less (e.g., 0.1 ppb by mass to 100 ppm by mass), and preferably 0.5 ppb by mass to 50 ppm by mass. These by-products are often produced as by-products in proportion to the second to third power of the acetaldehyde concentration.

In addition, the acetaldehyde and by-products derived from acetaldehyde form permanganate reducing compounds (PRCs). Therefore, it is preferred that, acetaldehyde, which is the main component of the by-products, be separated and removed from the reaction mixture, and useful components (e.g., methyl iodide etc.) be recovered from process stream and used effectively, it is also noted that $C_{2-12}$ alkyl iodides and the like, including methyl iodide, are also categorized as PRCs, but methyl iodide is not included in PRCs in the present specification.

Also, the reaction mixture may contain a metal, such as iron, nickel, chromium, manganese, or molybdenum, generated by the corrosion of the apparatus (hereinafter, also referred to as a "corrosive metal"), and other metals such as cobalt, zinc, and copper. The corrosive metal and other metals are also collectively referred to as a "corrosion metals". The total content of these impurities such as by-products and corrosion metals is, for example, 1 ppm by mass to 1 percent by mass with respect to the whole liquid phase of the reaction mixture. Thus, the process liquid in this acetic acid production process may contain, for example, approximately 1 ppm by mass to 1 percent by mass in total of the impurities. The concentration of the formic acid in the reaction mixture is, for example, 0 to 102 ppm by mass, preferably 0 to 85 ppm by mass, further preferably 0 to 50 ppm by mass, with respect to the whole liquid phase of the reaction mixture.

In the reactor 1 where the reaction mixture as described above is present, the reaction temperature is set to, for example, 150 to 250° C. The reaction pressure is set to the total pressure is set to, for example, 2.0 to 3.5 MPa (absolute pressure), and the carbon monoxide partial pressure is set to, for example, 0.4 to 1.8 MPa (absolute pressure), preferably 0.6 to 1.5 MPa (absolute pressure).

The vapor of a gas phase portion in the reactor 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reactor 1 through the line 13. The internal pressure of the reactor 1 can be controlled by the adjustment of the amount of the vapor withdrawn, and, for example, the internal pressure of the reactor 1 is kept constant. The vapor withdrawn from the reactor 1 is introduced to the condenser 1a.

The condenser 1a separates the vapor from the reactor 1 into a condensate and a gas by cooling and partial condensation. The condensate contains, for example, methyl iodide, hydrogen iodide, water, methyl acetate, acetic acid, dimethyl ether, methanol, acetaldehyde, formic acid, and propionic acid and is introduced to the reactor 1 from the condenser 1a through the line 14 and recycled. The gas contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. The gas discharged from the line 45 can be used as a CO source to be introduced to the bottom portion of the evaporator 2 mentioned later or the residue stream recycling lines 18 and 15.

In the reactor 1 during apparatus operation, as mentioned above, acetic acid is continuously produced. The reaction mixture containing such acetic acid is continuously withdrawn at a predetermined flow rate from the reactor 1 and introduced to the next evaporator 2 through the line 16.

In the present invention, it is preferred that the reaction step using the reactor 1 should satisfy the operating condition (i) involving a hydrogen partial pressure of less than 500 kPa (absolute pressure), a carbon dioxide partial pressure of less than 70 kPa (absolute pressure), and an operating temperature of more than 150° C. In this case, the hydrogen partial pressure (absolute pressure) can be less than 500 kPa and is preferably 400 kPa or less, more preferably 300 kPa or less, further preferably 200 kPa or less, and particularly preferably 150 kPa or less, in the carbonylation, hydrogen is formed by a reaction between carbon monoxide and water. This hydrogen increases the catalytic activity. Therefore, hydrogen may be fed to the reactor as necessary. Hydrogen may be fed by recycling gas component (containing hydrogen and carbon monoxide, etc.) discharged from downstream steps with being purified as necessary to the reactor. It is preferred that hydrogen having a low oxygen concentration be used as such hydrogen. Therefore, although the lower limit of the hydrogen partial pressure (absolute pressure) is 0 kPa, the hydrogen partial pressure (absolute pressure) may be more than 1 kPa (or more than 5 kPa). The carbon dioxide partial pressure (absolute pressure) can be less than 70 kPa and is preferably 60 kPa or less, more preferably 50 kPa or less, further preferably 40 kPa or less, and particularly preferably 30 kPa or less. The lower limit of the carbon dioxide partial pressure (absolute pressure) is 0 kPa, but may be 2 kPa (or 20 kPa). The operating temperature can be a temperature of more than 150° C. and is, for example, more than 160° C., preferably more than 175° C., more preferably 178° C. or more, further preferably 181° C. or more, and particularly preferably 184° C. or more. The upper limit of the operating temperature is, for example, 250° C., preferably 230° C., and more preferably 200° C. The reaction step using the reactor 1 satisfies the operating condition (i), whereby formic acid formation in the reactor 1 is suppressed. Furthermore, when a liquid containing formic acid is introduced to the reactor 1, the formic acid is efficiently decomposed.

The gas phase in the reaction step using the reactor 1 may satisfy the above (iii). The oxygen concentration in the gas phase of reactor 1 (gas phase withdrawn from line 13) is, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 percent by volume), and further preferably 500 ppb by volume to 500 ppm by volume (e.g., 1 to 100 ppm by volume). Further, when the gas phase in the reaction step satisfies the above (iii), the oxygen concentration is less than 7 percent by volume (e.g., 1 ppt by volume to 5 percent by volume), preferably 1 ppb by volume to 1 percent by volume (e.g., 10 ppb by volume to 0.5 percent by volume), more preferably 20 ppb by volume to 0.3 percent by volume, and further preferably 50 ppb by volume to 0.1 percent by volume (e.g., 100 ppb by volume to 200 ppm by volume).

The liquid phase in the reaction step using the reactor 1 may satisfy the above (iv). The oxygen concentration in the reaction mixture is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The condensate obtained by introducing vapor from the reactor 1 into the reactor 1 through the line 14 from the condenser 1a may satisfy the above (iv). The oxygen concentration in the condensate is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The gas (non-condensed gas fed to line 15) from condenser 1a may satisfy the above (iii). The oxygen concentration in the gas may be, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 percent by volume), and further preferably 500 ppb by volume to 500 ppm by volume (e.g., 1 to 100 ppm by volume). Also, when the gas satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residue stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residue stream is, for example, 80 to 200° C., preferably 100 to 180° C. The internal pressure of the evaporator is, for example, 50 to 1000 kPa (absolute pressure). The ratio between the vapor stream and the residue stream to be separated in the evaporation step is, for example, 10/90 to 50/50 (vapor stream/residue stream) in terms of a mass ratio. The vapor generated in this step contains, for example, methyl iodide, hydrogen iodide, water, methyl acetate, acetic acid, dimethyl ether, methanol, acetaldehyde, formic acid, and propionic acid and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The acetic acid concentration of the vapor stream is, for example 50 to 85 percent by mass, preferably 55 to 75 percent by mass. The residue stream generated in this step contains, for example, the catalyst and the co-catalyst (methyl iodide, lithium iodide, etc.) that had been contained in the reaction mixture, and water, methyl acetate, acetic acid, formic acid, and propionic acid remaining without being volatilized in this step, and is continuously introduced to the heat exchanger 2b from the evaporator 2 through the line 18 using the pump 57. The heat exchanger 2b cools the residue stream from the evaporator 2. The cooled residue stream is continuously introduced to the reactor 1 from the heat exchanger 2b through the line 19 and recycled. The line 18 and the line 19 are collectively referred to as residue stream recycling lines. Further, carbon monoxide may also be fed to the residue stream for suppressing sedimentation of the catalyst (not shown). The acetic acid concentration of the residue stream is, for example, 55 to 90 percent by mass, and preferably 60 to 85 percent by mass.

The condenser 2a separates the vapor stream from the evaporator 2 into a condensate and a gas by cooling and partial condensation. The condensate contains, for example, methyl iodide, hydrogen iodide, water, methyl acetate, acetic acid, dimethyl ether, methanol, acetaldenyde, formic acid, and propionic acid and is introduced to the reactor 1 from the condenser 2a through the lines 22 and 23 and recycled. The gas contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate generated by the cooling of this vapor in the condenser 2a is recycled to the reactor 1. Specifically, in this acetic acid production apparatus, heat generated through the methanol carbonylation is efficiently removed in the condenser 2a.

In the present invention, it is preferred that the evaporation step using the evaporator 2 should satisfy the operating condition (ii) involving a hydrogen partial pressure of 5 kPa or less (absolute pressure), a carbon dioxide partial pressure of less than 20 kPa (absolute pressure), and an operating temperature of more than 100° C. In this case, the hydrogen partial pressure (absolute pressure) is preferably 4 kPa or less, more preferably 3 kPa or less, further preferably 1 kPa or less, and particularly preferably 0.8 kPa or less. The lower limit of the hydrogen partial pressure (absolute pressure) is 0 kPa, but the lower limit may be set to be more than 0.0001 kPa. The carbon dioxide partial pressure (absolute pressure) is preferably 12 kPa or less more preferably 8 kPar further preferably 3 kPa or less, and particularly preferably 1 kPa or less. The lower limit of the carbon dioxide partial pressure (absolute pressure) is 0 kPa, but the lower limit may be set to be more than 0.0001 kPa. The operating temperature is preferably 112° C. or more, more preferably 120° C. or more, and further preferably 130° C. or more. The upper limit of the operating temperature is, for example, 260° C., preferably 200° C., more preferably 180° C. (or 170° C. or 160° C. Further, under such comparatively high temperature (and high pressure) conditions, hydrogen iodide tends to be formed, and depending on the oxygen concentration iodine also tends to be formed. However, in the present invention, even if hydrogen iodide is formed, formation of iodine can be effectively suppressed.

In the evaporation step that satisfies the operating condition (ii), the charge liquid to the evaporator 2 may have an acetic acid concentration of, for example, 50 to 90 percent by mass (preferably 60 to 80 percent by mass), a metal catalyst concentration (in terms of metal) of, for example, 200 to 10000 ppm by mass (preferably 300 to 5000 ppm by mass, and more preferably 400 to 2000 ppm by mass), a methyl iodide concentration of, for example, 1 to 20 percent by mass (preferably 5 to 15 percent by mass), an ionic iodide concentration of, for example, 1 to 25 percent by mass (preferably 5 to 20 percent by mass), a water concentration of, for example, 0.1 to 15 percent by mass (preferably 0.8 to 10 percent by mass), a methyl acetate concentration of, for example, 0.1 to 30 percent by mass (preferably 1 to 10 percent by mass), and a formic acid concentration of, for example, 10000 ppm by mass or less (preferably 0 to 1000 ppm by mass, more preferably 10 to 500 ppm by mass, further preferably 15 to 200 ppm by mass, particularly preferably 20 to 100 ppm by mass). The evaporation step using the evaporator 2 satisfies the operating conditions, whereby formic acid formation in the evaporator 2 is suppressed. Furthermore when a liquid containing formic acid is introduced to the evaporator 2, the formic acid is efficiently decomposed.

The gas phase in the evaporation step using the evaporator 2 may satisfy the above (iii). The oxygen concentrations in the vapor streams (lines 17 and 21) are respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when the gas phase in the evaporation step satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The liquid phase in the evaporation step using the evaporator 2 may satisfy the above (iv). The oxygen concentration in the residue stream is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The vapor stream from the evaporator 2 is separated into a condensate and a gas by cooling and partially condensing in the condenser 2a. The gas may be further separated into a condensate and a gas by cooling by another condenser, and the two condensates may be temporarily held in a single hold tank and subsequently recycled to the reactor 1 through a recycling line (not shown).

The condensate fed from the condenser 2a or the above-mentioned other condenser to the hold tank may satisfy the above (iv). The oxygen concentrations in the condensates are, respectively, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The gas fed from the condenser 2a to the above-mentioned other condenser and the gas obtained by separating with the above-mentioned other condenser may satisfy the above (iii). The oxygen concentration in the gas is, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 percent by volume), and further preferably 500 ppb by volume to 500 ppm by volume (e.g., 1 to 100 ppm by volume). Also, when the gases satisfy the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The distillation column 3 is a unit for performing the first distillation step and serves as the so-called light ends column in the present embodiment. The first distillation step is a step of separating and removing light ends by a distillation treatment of the vapor stream continuously introduced to the distillation column 3. More specifically, in the first distillation step, the vapor stream is separated by distillation into an overhead stream rich in at least one light ends selected from methyl iodide and acetaldehyde, and an acetic acid stream rich in acetic acid. The distillation column 3 consists of, for example, a rectification column such as a plate column or a packed column. In the case of adopting a plate column as the distillation column 3, the number of theoretical plates is, for example, 5 to 50, and the reflux ratio is, for example, 0.5 to 3000 according to the number of theoretical plates. In the inside of the distillation column 3, the column top pressure is set to, for example, 80 to 160 kPaG (gauge pressure), and the column bottom pressure is higher than the column top pressure and is set to, for example, 85 to 180 kPaG. In the inside of the distillation column 3, the column top temperature is, for example, a temperature of lower than the boiling point of acetic acid at the set column top pressure and is set to 90 to 130° C., and the column bottom temperature is, for example, a temperature of the boiling point of acetic acid or higher at the set column bottom pressure and is set to 120 to 165° C. (preferably 125 to 160° C.).

The vapor stream from the evaporator 2 is continuously introduced to the distillation column 3 through the line 21. From the column top portion of the distillation column 3, a vapor as the overhead stream is continuously withdrawn to the line 24. From the column bottom portion of the distillation column 3, a bottom liquid is continuously withdrawn to the line 25. 3b denotes a reboiler. From the height position between the column top portion and the column bottom portion of the distillation column 3, the acetic acid stream (first acetic acid stream; liquid) as a side stream is continuously withdrawn through the line 27.

The vapor withdrawn from the column top portion of the distillation column 3 contains a larger amount of components having a lower boiling point (light ends) than that of acetic acid as compared with the bottom liquid and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a through the line 24.

The condenser 3a separates the vapor from the distillation column 3 into a condensate and a gas by cooling and partial condensation. The condensate contains, for example, methyl iodide, hydrogen iodide, water, methyl acetate, acetic acid, dimethyl ether, methanol, acetaldehyde, and formic acid and is continuously introduced to the decanter 4 from the condenser 3a through the line 28. The condensate introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 through the line 29, and another portion of the aqueous phase is introduced to the reactor 1 through the lines 29, 30, and 23 and recycled. A portion of the organic phase is introduced to the reactor 1 through the lines 31 and 23 and recycled. Another portion of the organic phase and/or another portion of the aqueous phase is introduced to the acetaldehyde separation and removal system 9 through the lines 31 and 50 and/or the lines 30 and 51.

The gas phase in the light ends-removing step using the distillation column 3 may satisfy the above (iii). The oxygen concentration in the overhead stream (line 24) from the column top portion of the distillation column 3 and the oxygen concentration in the gas (line 32) not condensed in the condenser 3a are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when the light ends-removing step satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The condensate (line 28) condensed by the condenser 3a may satisfy the above (iv). The oxygen concentration in the condensate is similar to the oxygen concentration in the overhead stream from the column top portion of the distillation column 3.

The aqueous phase and the organic phase in the decanter 4 may satisfy the above (iv). The oxygen concentrations in the aqueous phase and the organic phase are, respectively, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The first acetic acid stream may satisfy the above (iv). The oxygen concentration in the first acetic acid stream is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The bottom liquid (line 25) may satisfy the above (iv). The oxygen concentration in the bottom liquid is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

In the distillation column 3, the overhead stream from the column top portion of the distillation column 6, a part of the overhead stream from the high-pressure absorption column, and the bottom portion stream from the low-pressure absorption column may be recycled (not shown).

In the present invention, it is preferred that the distillation step using the distillation column (light ends column) 3 should satisfy the operating condition (ii) involving a hydrogen partial pressure of 5 kPa or less (absolute pressure), a carbon dioxide partial pressure of less than 20 kPa (absolute pressure), and an operating temperature of more than 100° C. In this case, the hydrogen partial pressure (absolute pressure) is preferably 4 kPa or less, more preferably 3 kPa or less, and further preferably 1 kPa or less. The lower limit of the hydrogen partial pressure (absolute pressure) is 0 kPa, but the lower limit may be set to be more than 0.0001 kPa. The carbon dioxide partial pressure (absolute pressure) is preferably 12 kPa or less, more preferably 3 kPa or less, further preferably 3 kPa or less, and particularly preferably 1 kPa or less. The lower limit of the carbon dioxide partial pressure (absolute pressure) is 0 kPa, but the lower limit may be set to be more than 0.0001 kPa. The operating temperature is preferably 112° C. or more, and more preferably 114° C. or more. The upper limit of the operating temperature is, for example, 165° C., preferably 160° C., more preferably 150° C. (or 140° C. or 130° C.).

In the case where the distillation step using the distillation column (light ends column) 3 satisfies the operating condition (ii), the charge liquid to the distillation column 3 may have an acetic acid concentration of 30 percent by mass or more (e.g., 30 to 99.999 percent by mass) and a formic acid concentration of 5 ppm by mass or more (e.g., 5 to 10000 ppm by mass). Also, the charge liquid to the distillation column 3 has an acetic acid concentration of preferably 40 to 85 percent by mass (e.g., 50 to 85 percent by mass), and more preferably 50 to 75 percent by mass (e.g., 55 to 75 percent by mass), a methyl iodide concentration of preferably 2 to 50 percent by mass (e.g., 5 to 30 percent by mass), a water concentration of preferably 0.2 to 20 percent by mass (e.g., 1 to 15 percent by mass), a methyl acetate concentration of preferably 0.2 to 50 percent by mass (e.g., 2 to 30 percent by mass), and a formic acid concentration of preferably 5 to 10000 ppm by mass (e.g., 10 to 1000 ppm by mass, more preferably 10 to 500 ppm by mass, further preferably 15 to 200 ppm by mass, particularly preferably 20 to 100 ppm by mass). The distillation step using the distillation column 3 satisfies the operating condition (ii), whereby formic acid formation in the distillation column 3 is suppressed. In addition, when a liquid containing formic acid is fed to the distillation column 3, the formic acid is efficiently decomposed.

In the acetaldehyde-removing step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reactor 1 through the lines 52 and 23 and reused.

FIG. 2 is a schematic flow chart illustrating an acetaldehyde separation and removal system. According to this flow, in the case of treating, for example, the organic phase in the acetaldehyde-removing step, the organic phase is fed to a distillation column (first acetaldehyde-removing column) 91 through a line 101 and separated by distillation into an overhead stream rich in acetaldehyde (line 102) and a residue stream rich in methyl iodide (line 103). The overhead stream is condensed in a condenser 91a. A portion of the condensate is refluxed to the column top portion of the distillation column 91 (line 104), and the remainder of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde-removing column) 93 through a line 107 and separated by distillation into an overhead stream rich in acetaldehyde (line 112) and a residue stream rich in water (line 113). Then, the overhead stream rich in acetaldehyde is condensed in a condenser 93a. A portion of the condensate is refluxed to the column top portion of the distillation column 93 (line 114), and the remainder of the condensate is discharged to the outside of the system (line 115). The residue stream rich in methyl iodide, which is a bottom liquid of the first acetaldehyde-removing column 91, a raffinate rich in methyl iodide (line 108) obtained in the extraction column 92, and the residue stream rich in water, which is a bottom liquid of the second acetaldehyde-removing column 93 are recycled to the reactor 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 3 or discarded.

According to the flow of FIG. 2, in the case of treating the aqueous phase in the acetaldehyde-removing step, for example, the aqueous phase is fed to the distillation column (first acetaldehyde-removing column) 91 through the line 101 and separated by distillation into an overhead stream rich in acetaldehyde (line 102) and a residue stream rich in water (line 103). The overhead stream is condensed in the condenser 91a. A portion of the condensate is refluxed to the column top portion of the distillation column 91 (line 104), and the remainder of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde-removing column) 93 through the line 107 and separated by distillation into an overhead stream rich in acetaldehyde (line 112) and a residue stream rich in water (line 113). Then, the overhead stream rich in acetaldehyde is condensed in the condenser 93a. A portion of the condensate is refluxed to the column top portion of the distillation column 93 (line 114), and the remainder of the condensate is discharged to the outside of the system (line 115). The residue stream rich in water, which is a bottom liquid of the first acetaldehyde-removing column 91, a raffinate rich in methyl iodide (line 108) obtained in the extraction column 92, and the residue stream rich in water, which is a bottom liquid of the second acetaldehyde-removing column 93 are recycled to the reactor 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The aqueous phase or the organic phase fed to the distillation column 91 through the line 101 may satisfy the above (iv). The oxygen concentration in the aqueous phase or the organic phase is similar to the oxygen concentration in the aqueous phase or the organic phase in the decanter 4, respectively.

The liquid phase in the distillation step in the first acetaldehyde-removing column 91, the liquid phase in the extraction step in the extraction column 92, and the liquid phase in the distillation step in the second acetaldehyde-removing column 93 may each satisfy the above (iv). The oxygen concentration in the residue stream rich in water or methyl iodide (line 103), which is the bottom liquid of the first acetaldehyde-removing column 91, the oxygen concentration in the raffinate (line 108) rich in methyl iodide obtained by the extraction column 92, the oxygen concentration in the residue stream (line 113) rich in water, which is the bottom liquid of the second acetaldehyde-removing column 93, and the oxygen concentration in the extract (line 107) obtained by the extraction treatment in the extraction column 92 are, respectively, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The condensate (line 104) refluxed in the first acetaldehyde-removing column 91 and the condensate (line 114) refluxed in the second acetaldehyde-removing column 93 may each satisfy the above (iv). The oxygen concentration in the each condensate is similar to the oxygen concentrations in the overhead streams (lines 102, 112), respectively.

The distillation step in the first acetaldehyde-removing column 91, the extraction step in the extraction column 92, and the distillation step in the second acetaldehyde-removing column 93 may each satisfy the above (iii). The oxygen concentration in the overhead stream (line 102) from the column top portion of the first acetaldehyde-removing column 91, the oxygen concentration in the gas (line 106) not condensed in the condenser 91a, the oxygen concentration in the overhead stream (line 112) from the column top portion of the second acetaldehyde-removing column 93, and the oxygen concentration in the gas (line 116) not condensed in the condenser 93a, are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when each of the above-mentioned steps satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The acetaldehyde derived from the process stream containing at least the water, the acetic acid (AC), the methyl iodide (MeI), and the acetaldehyde (AD) can also be separated and removed by use of extractive distillation, as well as the method described above. For example, the organic phase and/or the aqueous phase (charge liquid) obtained by the separation of the process stream is fed to a distillation column (extractive distillation column). In addition, an extraction solvent (usually, water) is introduced to a concentration zone (e.g., space from the column top to the charge liquid feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably higher than the charge liquid feeding position, more preferably near the column top. The side stream withdrawal position is preferably lower than the extraction solvent introduction position and higher than the charge liquid feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentrations in the charge liquid and the bottom liquid (column bottom liquid). The ratio of acetaldehyde to methyl iodide in the side stream is larger than the ratio of acetaldehyde to methyl iodide in the charge liquid and the bottom liquid. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charge liquid feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charge liquid feeding position in the height direction of the column. Also, the miscible solvent introduction position is preferably lower than a recycle position in the case where the organic phase obtained by the separation of the side stream is recycled to this distillation column. The organic phase obtained by the separation of the side stream is recycled to the distillation column, or the miscible solvent is introduced to the distillation column whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The number of theoretical plates of the distillation column (extractive distillation column) is, for example, 1 to 100, preferably 2 to 50, more preferably 3 to 30, and further preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charge liquid (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, and further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow chart illustrating an acetaldehyde separation and removal system using the extractive distillation, according to an embodiment. In this example, the organic phase and/or the aqueous phase (charge liquid) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed higher than the charge liquid feeding position of the distillation column 94. In this extractive distillation, preferably the whole amount of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases and liquid-liquid separation is conducted in a decanter 96. The aqueous phase in the decanter 96 is fed to a distillation column 97 (acetaldehyde-removing column) through a line 216 and distilled. The vapor at the column top is introduced to a condenser 97a through a line 217 and condensed. A portion of the condensate (mainly, acetaldehyde and methyl iodide) is refluxed to the column top of the distillation column 97, and the remainder is discarded or fed to a distillation column 98 (extractive distillation column) through a line 220. Water is introduced thereto from near the column top of the distillation column 98 through a line 222, followed by extractive distillation. The vapor at the column top is introduced to a condenser 98a through a line 223 and condensed. A portion of the condensate (mainly, methyl iodide) is refluxed to the column top portion, and the remainder is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charge liquid), a solvent (acetic acid, ethyl acetate, etc.) miscible with the components (e.g., methyl acetate) constituting the organic phase obtained by the separation of the process stream may be charged into the distillation column 94 through a line 215 to thereby improve distillation efficiency. The feeding position of the miscible solvent to the distillation column 54 is higher than the charge liquid feeding portion (junction of the line 201) and lower than the junction of the recycling line 210. A bottom liquid of the distillation column 94 is recycled to the reaction system. A vapor at the column top of the distillation column 94 is introduced to a condenser 94a through a line 203 and condensed. The condensate is separated in a decanter 95. The organic phase is refluxed to the column top portion of the distillation column 54 through a line 206, while the aqueous phase is introduced to the decanter 95 through a line 207. A bottom liquid (water is a main component) of the distillation column 97 and a bottom liquid (water containing a small amount of acetaldehyde) of the distillation column 98 (extractive distillation column) are discharged to the outside of the system through lines 218 and 224, respectively, or recycled to the reaction system. A gas that has not been condensed in the condenser 94a, 97a, or 98a (line 211, 221, or 227) is subjected to absorption treatment in the scrubber system 8, or discarded.

FIG. 4 is a schematic flow chart illustrating an acetaldehyde separation and removal system using the extractive distillation, according to another embodiment. In this example, a condensate of a vapor from the column top of the distillation column 94 is introduced to a hold tank 100, and the whole amount thereof is refluxed to the column top portion of the distillation column 94 through the line 206. The other points are the same as in the example of FIG. 3.

FIG. 5 is a schematic flow chart illustrating an acetaldehyde separation and removal system using the extractive distillation, according to yet another embodiment. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

The aqueous phase or the organic phase fed to the distillation column 94 through the line 201 may satisfy the above (iv). The oxygen concentration in the aqueous phase or the organic phase is similar to the oxygen concentration in the aqueous phase or the organic phase in the decanter 4, respectively.

The liquid phase in the distillation step in the distillation column 94, the liquid phase in the distillation step in the distillation column 97, and the liquid phase in the distillation step in the distillation column 98 may each satisfy the above (iv). The oxygen concentration in the bottom liquid (line 218) of the distillation column 97, the oxygen concentration in the bottom liquid (line 224) of the distillation column 98, the oxygen concentration in the condensate (line 205) condensed in the condenser 94a, the oxygen concentrations in the aqueous phase and the organic phase in the decanter 99, the oxygen concentration in the organic phase (line 206) refluxed to the distillation column 94, the oxygen concentration in the aqueous phase (line 207) fed to the decanter 95, the oxygen concentrations in the aqueous phase and the organic phase in the decanter 95, the oxygen concentration in the aqueous phase (line 212) fed to the condenser 95a, the oxygen concentrations in the aqueous phase and the organic phase in the decanter 96, the oxygen concentration in the aqueous phase fed to the distillation column 97, the oxygen concentration in the liquid phase (line 219) condensed in the condenser 97a and refluxed to the distillation column 57, the oxygen concentration in the liquid phase (line 220) fed to the distillation column 98, the oxygen concentration in the liquid phase (line 225) condensed in the condenser 98a and refluxed to the distillation column 98, the oxygen concentrations in the liquid phases (lines 20S, 213, and 214) that can be recycled to the distillation column 94, the oxygen concentration in the bottom liquid (line 204) of the distillation column 94, the oxygen concentration in the bottom liquid (line 218) of the distillation column 97, and the oxygen concentration in the bottom liquid (line 224) of the distillation column 98 are, respectively, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The gas phase in the distillation step in the distillation column 94, the distillation step in the distillation column 97, and the distillation step in the distillation column 98 may each satisfy the above (iii). The oxygen concentration in the overhead stream (line 203) from the column top portion of the distillation column 94, the oxygen concentration in the gas (line 211) not condensed in the condenser 94a, the oxygen concentration in the overhead stream (line 217) from the column top portion of the distillation column 97, the oxygen concentration in the gas (line 221) not condensed in the condenser 97a, the oxygen concentration in the overhead stream (line 223) from the column top portion of the distillation column 98, and the oxygen concentration in the gas (line 227) not condensed in the condenser 98a, are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when each of the above-mentioned steps satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

Further, the organic phase and/or aqueous phase separated by the decanter 4 may be introduced to an alkane separation step (not shown). In the alkane separation step, alkanes contained in the organic phase and/or aqueous phase are separated and removed by a known method such as distillation. For example, the organic phase is fed to a distillation column (alkane-removing column) for performing the alkane separation step and distilled, and is separated into an overhead stream from the column top portion or an upper portion of the alkane-removing column and a bottom portion stream. A part of the bottom portion stream containing alkanes is heated and recycled to the alkane-removing column, and the remainder is fed to an incineration unit for incineration. On the other hand, the overhead stream, which contains acetaldehyde and methyl iodide, is cooled and condensed by the condenser, and stored in a tank as a condensate. A part of the condensate is refluxed to the alkane-removing column, and the remainder of condensate is recycled to the reactor.

The aqueous phase or the organic phase fed to the alkane-removing column may satisfy the above (iv). The oxygen concentration in the aqueous phase or the organic phase is similar to the oxygen concentration in the aqueous phase or the organic phase in the decanter 4, respectively.

The liquid phase in the alkane separation step may satisfy the above (iv). The oxygen concentration in the bottom liquid of the alkane-removing column, the oxygen concentration in the liquid phase refluxed and condensed by the condenser from the overhead stream from the alkane-removing column, and the oxygen concentration in the bottom liquid of the alkane-removing column are each, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The gas phase in the alkane separation step may satisfy the above (iii). The overhead stream from the alkane-removing column and the gas not condensed in the condenser for cooling the overhead stream are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when the alkane separation step satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

In FIG. 1 described above, the gas generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gas that has entered the scrubber system 8 are absorbed to an absorbing solvent in the scrubber system 8. The hydrogen iodide generates methyl iodide through reaction with methanol or methyl acetate in the absorbing solvent. Then, a liquid portion containing useful components such as the methyl iodide is recycled to the reactor 1 from the scrubber system 8 through the recycling lines 48 and 23 and reused.

The bottom liquid withdrawn from the column bottom portion of the distillation column 3 contains a larger amount of components having a higher boiling point (heavy ends) than that of acetic acid as compared with the overhead stream and the side stream from the distillation column 3 and contains, for example, propionic acid, and the above-mentioned catalyst and co-catalyst entrained in droplets. This bottom liquid also contains, for example, acetic acid, methyl iodide, methyl acetate, and water. In the present embodiment, a portion of such a bottom liquid is continuously introduced to the evaporator 2 through the lines 25 and 26 and recycled, and another portion of the bottom liquid is continuously introduced to the reactor 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9 percent by mass, preferably 93 to 99 percent by mass. Also, the first acetic acid stream may contain, in addition to acetic acid, for example, methyl iodide, hydrogen iodide, water, methyl acetate, dimethyl ether, methanol, acetaldehyde, formic acid, and propionic acid. The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. The first acetic acid stream withdrawn as the side stream of the distillation column 3 and the column bottom liquid of the distillation column 3 or the condensate of the vapor at the column bottom portion of the distillation column 3 may be used as is as the acetic acid product, or may be directly introduced to the distillation column 6 without going through the distillation column 5. A part of the first acetic acid stream may also be returned to the distillation column 3 (not shown).

To the first, acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added into the process also reacts with acetic acid to form potassium acetate.

The aqueous solution of potassium hydroxide that is fed or added to the first acetic acid stream may satisfy the above (iv). The oxygen concentration in the potassium hydroxide aqueous solution is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. The distillation column 5 consists of, for example, a rectification column such as a plate column or a packed column. In the case of adopting a plate column as the distillation column 5, the number of theoretical plates thereof is, for example, 5 to 50, and the reflux ratio is, for example, 0.1 to 3000 according to the number of theoretical plates. In the inside of the distillation column 5 in the second distillation step, the column top pressure is set to, for example, 10 to 500 kPaG, and preferably 150 to 250 kPaG, and the column bottom pressure is higher than the column top pressure and is set to, for example, 130 to 310 kPaG, and preferably 160 to 290 kPaG. In the inside of the distillation column 5 in the second distillation step, the column top temperature is, for example, a temperature of higher than the boiling point of water and lower than the boiling point of acetic acid at the set column top pressure and is set to 130 to 175° C., and the column bottom temperature is, for example, a temperature of the boiling point of acetic acid or higher at the set column bottom pressure and is set to 150 to 185° C.

A vapor as an overhead stream is continuously withdrawn to the line 33 from the column top portion of the distillation column 5. A bottom liquid is continuously withdrawn to the line 34 from the column bottom portion of the distillation column 5. 5b denotes a reboiler. A side stream (liquid or gas) may be continuously withdrawn to the line 34 from the height position between the column top portion and the column bottom portion of the distillation column 5.

The vapor withdrawn from the column top portion of the distillation column 5 contains a larger amount of components having a lower boiling point (light ends) than that of acetic acid as compared with the bottom liquid from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a through the line 33.

The condenser 5a separates the vapor from the distillation column 5 into a condensate and a gas by cooling and partial condensation. The condensate contains, for example, water and acetic acid. A portion of the condensate is continuously refluxed to the distillation column 5 from the condenser 5a through the line 35. Another portion of the condensate is continuously introduced to the reactor 1 from the condenser 5a through the lines 35, 36, and 23 and recycled. The gas generated in the condenser 5a contains for example, carbon monoxide, hydrogen, methane, carbon dioxide, nitrogen, oxygen, methyl iodide, hydrogen iodide water, methyl acetate, acetic acid, dimethyl ether, methanol, acetaldehyde, and formic acid and is fed to the scrubber system 8 from the condenser 5a through the lines 37 and 15. Hydrogen iodide in the gas that has entered the scrubber system 8 is absorbed to an absorbing solvent in the scrubber system 8. Methyl iodide is generated through the reaction of the hydrogen iodide with methanol or methyl acetate in the absorbing solvent. Then, a liquid portion containing useful components such as the methyl iodide is recycled to the reactor 1 from the scrubber system 8 through the recycling lines 48 and 23 and reused.

The gas phase in the dehydration step using the distillation column 5 may satisfy the above (iii). The oxygen concentration in the overhead stream (line 33) from the column top portion of the distillation column 5 and the oxygen concentration in the gas (line 45) not condensed in the condenser 6a are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when the gas phase in the dehydration step satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The bottom liquid (or side stream) withdrawn from the column bottom portion of the distillation column 5 contains more of a component having a higher boiling point (heavy ends) than that of acetic acid than the overhead stream from the distillation column 5. This heavy ends includes, for example, propionic acid, potassium acetate (when potassium hydroxide has been fed to the line 27 etc.), and the above-mentioned catalyst and co-catalyst entrained in droplets. This bottom liquid can also contain acetic acid. Such a bottom liquid is continuously introduced into the next distillation column 6 as a second acetic acid stream through the line 34.

The second acetic acid stream (bottom liquid of the distillation column 5, line 34) may satisfy the above (iv). The oxygen concentration in the second acetic acid stream is, for example, 10 percent, by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

In the distillation column 5, methanol may be added to one or a plurality of places in the distillation column 5 to convert hydrogen iodide contained in the first acetic acid stream into methyl iodide and withdraw it as the overhead stream from the line 33 (not shown).

In the present invention, it is preferred that the distillation step using the distillation column (dehydration column) 5 should satisfy the operating condition (ii) involving a hydrogen partial pressure of 5 kPa or less (absolute pressure), a carbon dioxide partial pressure of less than 20 kPa (absolute pressure), and an operating temperature of more than 100° C. In this case, the hydrogen partial pressure (absolute pressure) is preferably 2 kPa or less, more preferably 1 kPa or less, and further preferably 0.5 kPa or less. The lower limit of the hydrogen partial pressure (absolute pressure) is 0 kPa, but the lower limit may be set to be more than 0.0001 kPa. The carbon dioxide partial pressure (absolute pressure) is preferably 5 kPa or less, more preferably 2 kPa or less, and further preferably 1 kPa or less (e.g., 0.5 kPa or less). The lower limit of the carbon dioxide partial pressure (absolute pressure) is 0 kPa, but the lower limit may be set to be more than 0.0001 kPa. The operating temperature is preferably 120° C. or more, and more preferably 130° C. or more. The upper limit of the operating temperature is, for example, 170° C., preferably 165° C., more preferably 160° C., and further preferably 155° C.

In the case where the distillation step using the distillation column (dehydration column) 5 satisfies the operating condition (ii), the charge liquid to the distillation column 5 may have an acetic acid concentration of 30 percent by mass or more (e.g., 30 to 99.999 percent by mass) and a formic acid concentration of 5 ppm by mass or more (e.g., 5 to 10000 ppm by mass). Also, the charge liquid to the distillation column 5 has an acetic acid concentration of preferably 80 to 99.9 percent by mass (e.g., 90 to 99.5 percent by mass, particularly, 93 to 99 percent by mass), a methyl iodide concentration of preferably 0.01 to 16 percent by mass (e.g., 0.1 to 8 percent by mass, particularly, 0.2 to 5 percent by mass), a water concentration of preferably 0.05 to 18 percent by mass (e.g., 0.1 to 8 percent by mass, particularly, 0.2 to 5 percent by mass), a methyl acetate concentration of preferably 0.01 to 16 percent by mass (e.g., 0.1 to 8 percent by mass, particularly, 0.2 to 5 percent by mass), and a formic acid concentration of preferably 5 to 10000 ppm by mass (e.g., 10 to 1000 ppm by mass, more preferably 10 to 500 ppm by mass, further preferably 15 to 200 ppm by mass, and particularly preferably 20 to 100 ppm by mass). The distillation step using the distillation column 5 satisfies the operating condition (ii), whereby formic acid formation in the distillation column 5 is suppressed. In addition, when a liquid containing formic acid is fed to the distillation column 5, the formic acid is efficiently decomposed.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99 percent by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide. The oxygen concentration in the second acetic acid stream after feeding or adding potassium hydroxide by the potassium hydroxide introducing line is the same as that in the second acetic acid stream (bottom liquid of distillation column 5).

The distillation column 6 is a unit for performing the third distillation step and serves as the so-called heavy ends column in the present embodiment. The third distillation step is a step for further purifying acetic acid by the purification treatment of the second acetic acid stream continuously introduced to the distillation column 6. The distillation column 6 consists of, for example, a rectification column such as a plate column or a packed column. In the case of adopting a plate column as the distillation column 6, the number of theoretical plates thereof is, for example, 5 to 50, and the reflux ratio is, for example, 0.2 to 3000 according to the number of theoretical plates. In the inside of the distillation column 6 in the third distillation step, the column top pressure is set to, for example, −100 to 150 kPaG, and the column bottom pressure is higher than the column top pressure and is set to, for example, −90 to 180 kPaG. In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top portion of the distillation column 6. A bottom liquid is continuously withdrawn to the line 39 from the column bottom portion of the distillation column 6. 6b denotes a reboiler. A side stream (liquid or gas) is continuously withdrawn to the line 46 from the height position between the column top portion and the column bottom portion of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top portion of the distillation column 6 contains a larger amount of components having a lower boiling point (light ends) than that of acetic acid as compared with the bottom liquid from the distillation column 6, and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate and a gas by cooling and partial condensation. The condensate contains, in addition to acetic acid, for example, methyl iodide, hydrogen iodide, water, methyl acetate, dimethyl ether, methanol, and formic acid. At least a portion of the condensate is continuously refluxed to the distillation column 6 from the condenser 6a through the line 40. A portion (distillate) of the condensate may be recycled to the first acetic acid stream in the line 27 before introduction to the distillation column 5 from the condenser 6a through the lines 40, 41, and 42. Together with this or instead of this, a portion (distillate) of the condensate may be recycled to the vapor stream in the line 21 before introduction to the distillation column 3 from the condenser 6a through the lines 40, 41, and 43. Also, a portion (distillate) of the condensate may be recycled to the reactor 1 from the condenser 6a through the lines 40, 44, and 23. Furthermore, as mentioned above, a portion of the distillate from the condenser 6a may be fed to the scrubber system 8 and used as an absorbing solvent in this system. In the scrubber system 8, a gas after absorption of a useful portion is discharged to the outside of the apparatus. Then, a liquid portion containing the useful components is introduced or recycled to the reactor 1 from the scrubber system 8 through the recycling lines 48 and 23 and reused. In addition, a portion of the distillate from the condenser 6a may be introduced to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate is removed from the distillation treatment system in the distillation column 6, the amount of the distillate (distillate amount) is, for example, 0.01 to 30 percent by mass, preferably 0.1 to 10 percent by mass, more preferably 0.3 to 5 percent by mass, more preferably 0.5 to 3 percent by mass, of the condensate generated in the condenser 6a. On the other hand, the gas generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The gas phase in the heavy ends-removing step using the distillation column 6 may satisfy the above (iii). The oxygen concentration in the overhead stream (line 38) from the column top portion of the distillation column 6 is, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when the gas phase in the heavy ends-removing step satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The bottom liquid withdrawn from the column bottom portion of the distillation column 6 through the line 39 contains a larger amount of components having a higher boiling point (heavy ends) than that of acetic acid as compared with the overhead stream from the distillation column 6 and contains, for example, propionic acid, acetic anhydride, and potassium acetate (in the case of feeding potassium hydroxide to the line 34, etc.). Also, the bottom liquid withdrawn from the column bottom portion of the distillation column 6 through the line 39 also contains, for example, corrosion metals such as a metal formed at and released from the inside wall of a member constituting this acetic acid production apparatus and a compound of iodine derived from corrosive iodine and the corrosion metals, etc. In the present embodiment such a bottom liquid is discharged to the outside of the acetic acid production apparatus.

The bottom liquid (line 39) may satisfy the above (iv). The oxygen concentration in the bottom liquid is, for example, 10 percent by volume or less (e.g., 0.1 ppb by volume to 10 percent by volume), preferably 0.2 ppb by volume to 3.6 percent by volume (e.g., 1 ppb by volume to 2 percent, by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999 percent by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

The third acetic acid stream (line 46) may satisfy the above (iv). The oxygen concentration in the third acetic acid stream is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

In the present invention, it is preferred that the distillation step using the distillation column (heavy ends column) 6 should satisfy the operating condition (ii) involving a hydrogen partial pressure of 5 kPa or less (absolute pressure), a carbon dioxide partial pressure of less than 20 kPa (absolute pressure), and an operating temperature of more than 100° C. In this case, the hydrogen partial pressure (absolute pressure) is preferably 2 kPa or less, more preferably 1 kPa or less, and further preferably 0.5 kPa or less. The lower limit of the hydrogen partial pressure (absolute pressure) is 0 kPa, but the lower limit may be set to be more than 0.0001 kPa. The carbon dioxide partial pressure (absolute pressure) is preferably 5 kPa or less, more preferably 2 kPa or less, and further preferably 1 kPa or less (e.g., 0.5 kPa or less). The lower limit of the carbon dioxide partial pressure (absolute pressure) is 0 kPa, but the lower limit may be set to be more than 0.0001 kPa. The operating temperature is preferably 120° C. or more, and more preferably 130° C. or more. The upper limit of the operating temperature is, for example, 165° C., preferably 160° C., further preferably 155° C.

In the case where the distillation step using the distillation column (heavy ends column) 6 satisfies the operating condition (ii), the charge liquid to the distillation column 6 has an acetic acid concentration of preferably 99.1 to 99.999 percent by mass and a formic acid concentration of preferably 5 to 9000 ppm by mass (e.g., 10 to 1000 ppm by mass, more preferably 10 to 500 ppm by mass, further preferably 15 to 200 ppm by mass, particularly preferably 20 to 100 ppm by mass). The distillation step using the distillation column 6 satisfies the operating condition (ii), whereby formic acid formation in the distillation column 6 is suppressed. In addition, when a liquid containing formic acid is fed to the distillation column 6, the formic acid is efficiently decomposed.

The ion exchange resin column 7 is a purification unit for performing the adsorptive removing step. This adsorptive removing step is a step for further purifying acetic acid by the adsorptive removal of, mainly, alkyl iodides (hexyl iodide, decyl iodide, etc.) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removing step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removing step, the internal temperature is, for example, 18 to 100° C., and the flow rate of the acetic acid stream [the throughput of acetic acid per $m^3$ resin volume ($m^3/h$)] is, for example, 3 to 15 $m^3/h \cdot m^3$ (resin volume).

A fourth acetic acid stream is continuously brought from a lower end portion of the ion exchange resin column 7 to the line 47. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999 percent by mass, or more, as long as being higher than the acetic acid concentration of the third acetic acid stream. In this production method, this fourth acetic acid stream can be retained in a product tank (not shown).

The fourth acetic acid stream may satisfy the above (iv). The fourth acetic acid stream has a similar oxygen concentration to the oxygen concentration in the third acetic acid stream.

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a rectification column such as a plate column or a packed column. In the case of adopting a plate column as the product column, the number of theoretical plates thereof is, for example, 5 to 50, and the reflux ratio is, for example, 0.5 to 3000 according to the number of theoretical plates. In the inside of the product column in the purification step, the column top pressure is set to, for example, −195 to 150 kPaG, and the column bottom pressure is higher than the column top pressure and is set to, for example, −190 to 180 kPaG. In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of light ends (e.g., methyl iodide, water, methyl acetate, dimethyl ether, crotonaldehyde, acetaldehyde, and formic acid) is continuously withdrawn from the column top portion of such a product column. This vapor is separated into a condensate and a gas in a predetermined condenser. A portion of the condensate is continuously refluxed to the product column, and another portion of the condensate may be recycled to the reactor 1 or discarded to the outside of the system, or both. The gas is fed to the scrubber system 8. A bottom liquid containing a very small amount of heavy ends is continuously withdrawn from the column bottom portion of the product column. This bottom liquid is recycled to, for example, the second acetic acid stream in the line 34 before introduction to the distillation column 6. A side stream (liquid) is continuously withdrawn as a fifth acetic acid stream from the height position between the column top portion and the column bottom portion of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column.

Specifically, the acetic acid concentration of the fifth acetic acid stream is higher than the acetic acid concentration of the fourth acetic acid stream. The acetic acid concentration of the fifth acetic acid stream is, for example, 99.9 to 99.999 percent by mass, or more, as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

The gas phase in the product step using the product column may satisfy the above (iii). The oxygen concentration in the overhead stream from the column top portion of the product column and the oxygen concentration in the condensate refluxed to the product column are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 percent by volume), and further preferably 500 ppb by volume to 500 ppm by volume (e.g., 1 to 100 ppm by volume). Also, when the gas phase in the product step satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The gas separated from the overhead stream from the column top portion of the product column may satisfy the above (iii). The oxygen concentration in the gas may be, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 percent by volume), and further preferably 500 ppb by volume to 500 ppm by volume (e.g., 1 to 100 ppm by volume). Also, when the gas satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The fifth acetic acid stream and the bottom liquid may satisfy the above (iv). The oxygen concentration in the fifth acetic acid stream is, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppt by volume to 500 ppm by volume), and particularly preferably 10 ppt by volume to 300 ppm by volume (e.g., 100 ppt by volume to 100 ppm by volume).

In the present invention, it is preferred that the distillation step using the distillation column (product column) should satisfy the operating condition (ii) involving a hydrogen partial pressure of 5 kPa or less (absolute pressure), a carbon dioxide partial pressure of less than 20 kPa (absolute pressure), and an operating temperature of more than 100° C. In this case, the hydrogen partial pressure (absolute pressure) is preferably 2 kPa or less, more preferably 1 kPa or less, and further preferably 0.5 kPa or less. The lower limit of the hydrogen partial pressure (absolute pressure) is 0 kPa, but the lower limit may be set to be more than 0.0001 kPa. The carbon dioxide partial pressure (absolute pressure) is preferably 5 kPa or less, more preferably 2 kPa or less, and further preferably 1 kPa or less (e.g., 0.5 kPa or less). The lower limit of the carbon dioxide partial pressure (absolute pressure) is 0 kPa, but the lower limit may be set to be more than 0.0001 kPa. The operating temperature is preferably 120° C. or more, and more preferably 130° C. or more. The upper limit of the operating temperature is, for example, 165° C., preferably 160° C., and more preferably 155° C.

In the case where the distillation step using the distillation column (product column) satisfies the operating condition (ii), the charge liquid to the distillation column (product column) has an acetic acid concentration of preferably 99.8 to 99.999 percent by mass and a formic acid concentration of preferably 5 to 2000 ppm by mass (e.g., 5 to 1000 ppm by mass, preferably 5 to 100 ppm by mass). The distillation step using the distillation column (product column) satisfies the operating condition (ii), whereby formic acid formation in the distillation column (product column) is suppressed. In addition, when a liquid containing formic acid is fed to the distillation column (product column), the formic acid is efficiently decomposed.

In the scrubber system 8, useful components (e.g., methyl iodide, water, methyl acetate, acetic acid, etc.) are separated and recovered from the gas generated by the acetic acid production process. For this separation and recovery, in the present embodiment, a wet method is used in which an absorbing solvent is used to collect the useful components in the gas. The absorbing solvent is preferably an absorbing solvent containing at least acetic acid and/or methanol. The absorbing solvent may contain methyl acetate. For example, the condensate of the vapor from distillation column 6 can be used as the absorbing solvent. The separation and recovery may be carried out by employing a pressure swing adsorption process. The separated, recovered useful components (such as methyl iodide) are introduced and recycled from the scrubber system 8 through the recycling line 48 to the reactor 1. The gas after the collection of useful components is discarded through the line 49. The treatment in the scrubber system 8, subsequent recycling to the reactor 1, and discarding are also applicable to the above-mentioned gas fed from other condensers to the scrubber system 8. The production method of the present invention preferably includes a scrubbing step of subjecting an off-gas from the process to an absorbing treatment with an absorbing solvent, which contains at least acetic acid, to separate the off-gas into a carbon monoxide-rich stream and an acetic acid-rich stream.

The scrubber system 8 may include, for example, a step of absorbing off-gas at high pressure in an absorbing solvent (high-pressure absorption step), a step of absorbing off-gas at low pressure in an absorbing solvent, and a step of desorbing the gas components that have been absorbed in the high-pressure absorption step and the low-pressure absorption step (desorption step).

In the high-pressure absorption step, the gas (off-gas rich in carbon monoxide and methyl iodide) from the reactor 1 is scrubbed by being brought into contact with acetic acid as an absorbing solvent in the high-pressure absorption column, and separated into an overhead stream rich in carbon monoxide and a bottom portion stream rich in methyl iodide, methyl acetate, and water. A part of the overhead stream is fed to the evaporator 2, and the remainder is fed to the boiler and used as a process heat source or is discharged to the atmosphere by a flare stack or a vent stack. The overhead stream remainder may be incinerated or recovered. The bottom portion stream is fed to a desorption column.

In the low-pressure absorption step, the gas that did not condense in the condenser 3a of the light ends-removing step and the gas (off-gas enriched with acetic acid, methyl iodide, and methyl acetate) from the evaporator 2 merge together to form a mixture, which is then brought into contact and scrubbed with acetic acid as an absorbing solvent in a low-pressure absorption column, separated into an overhead stream rich in carbon monoxide, carbon dioxide, and nitrogen and a bottom portion stream rich in acetic acid, methyl iodide, and methyl acetate. The overhead stream merges with the overhead stream of the high-pressure absorption column, fed to the boiler as a mixed gas, and used as a heat source for the process. A part of the bottom portion stream is merged with a part of the bottom portion stream of the high-pressure absorption column, and fed to the evaporator 2, and the remainder of the bottom portion stream is merged with the bottom portion stream of the high-pressure absorption column, and fed to the desorption column as a mixed acetic acid stream.

In the desorption step, the mixed acetic acid stream is distilled and stripped in the desorption column (stripping column), and separated into an overhead stream rich in methyl iodide and acetic acid (including methyl acetate, acetaldehyde, etc.), and a bottom portion stream rich in acetic acid, methyl acetate, and water. A first part of the bottom portion stream is heated by the heating unit and returned to a lower portion of the desorption column. Also, a second part (or the remainder) of the bottom portion stream is merged and mixed with a part of the condensate of the overhead stream of the distillation column 6, and a part of this mixed liquid is recycled to the upper part of the high-pressure absorption column. The remainder of the mixed liquid may also be recycled to the upper part of the low-pressure absorption column. The overhead stream is cooled and condensed by the condenser. The gas (gas rich in methyl iodide and carbon monoxide and also containing carbon dioxide, methane, ethyl acetate, acetaldehyde, etc.) may also be merged with the gas of the decanter 4 or the gas of the vapor stream 17 from the evaporator 2, and cooled and condensed by the condenser. The condensate (condensate rich in methyl iodide, acetic acid, and methyl acetate, and containing water, acetaldehyde, etc.) of the overhead stream may be recycled to the reactor 1.

The gas phase in the high-pressure absorption step, the low-pressure absorption step, and the desorption step may each satisfy the above (iii). The oxygen concentration in the overhead stream from the high-pressure absorption column, the oxygen concentration in the overhead stream from the low-pressure absorption column, the oxygen concentration in the overhead stream from the desorption column, and the oxygen concentration in the gas not condensed by cooling by the condenser of these overhead streams are, respectively, for example, 10 percent by volume or less (e.g., 10 ppb by volume to 10 percent by volume), preferably 10 ppb by volume to 3.6 percent by volume (e.g., 20 ppb by volume to 2 percent by volume), more preferably 30 ppb by volume to 1 percent by volume (e.g., 100 ppb by volume to 0.1 ppm by volume), and further preferably 500 ppb by volume to 500 ppm by volume (e.g., 1 to 100 ppm by volume). Also, when the gas phase in each of the above-mentioned steps satisfies the above (iii), the oxygen concentration is less than 7 percent by volume (e.g., 1 ppt by volume to 5 percent by volume), preferably less than 3.6 percent by volume (e.g., 0.1 ppb by volume to 2 percent by volume), more preferably 1 ppb by volume to 1 percent by volume (e.g., 10 ppb by volume to 0.5 percent by volume), further preferably 20 ppb by volume to 0.3 percent by volume, and particularly preferably 50 ppb by volume to 0.1 percent by volume (e.g., 100 ppb by volume to 200 ppm by volume).

The high-pressure absorption step, the low-pressure absorption step, and the desorption step may each satisfy the above (iv). The oxygen concentrations in the bottom portion stream of the high-pressure absorption column, the bottom portion stream of the low-pressure absorption column, the bottom portion stream of the desorption column, and the condensate condensed by the condenser of the overhead stream from the desorption column are, respectively, for example, 10 percent by volume or less (e.g., 0.1 ppb by volume to 10 percent by volume), preferably 0.2 ppb by volume to 3.6 percent by volume (e.g., 1 ppb by volume to 2 percent by volume), more preferably less than 1 percent by volume (e.g., 1 ppt by volume to 1000 ppm by volume), further preferably less than 700 ppm by volume (e.g., 1 ppb by volume to 500 ppm by volume), and particularly preferably 10 ppt by volume to 300 ppm by volume (e.g., 100 ppt by volume to 100 ppm by volume).

In the embodiments described above, it is preferred that, as mentioned above, the retention time in the step that satisfies the operating condition (i) or the step that satisfies the operating condition (ii) should be 1 minute or more (e.g., 2 minutes or more, preferably 3 minutes or more, more preferably 5 minutes or more, particularly preferably 10 minutes or more). The upper limit of the retention time is, for example, 2 hours, preferably 1 hour.

Also, a process liquid having a formic acid concentration of 10 ppm by mass or more (e.g., 10 to 10000 ppm by mass, preferably 15 to 1000 ppm by mass, further preferably 20 to 200 ppm by mass) may be recycled to a step that satisfies (v) operating conditions involving a hydrogen partial pressure of less than 500 kPa (absolute pressure), a carbon dioxide partial pressure of less than 70 kPa (absolute pressure), and an operating temperature of more than 100° C. Examples of the step that satisfies the operating condition (v) include the reaction step, the evaporation step, and the distillation steps (e.g., the light ends-removing step and the dehydration step). The step that satisfies the operating condition (v) includes the step that satisfies the operating condition (i) and the step that satisfies the operating condition (ii). The process liquid having a formic acid concentration of 10 ppm by mass or more is recycled to the step that satisfies the operating condition (v) so that the formic acid contained in the process liquid is efficiently decomposed in this step.

Furthermore, an overhead liquid of the distillation column in at least one distillation step, for example, the light ends-removing step, the dehydration step, the heavy ends-removing step, or the product step may be recycled to the step that satisfies the operating condition (i) or the step that satisfies the operating condition (ii). Examples of the step that satisfies the operating condition (i) and the step that satisfies the operating condition (ii) include the reaction step, the evaporation step, the light ends-removing step, and the dehydration step. In this case, it is preferred that the step to which the overhead liquid of the distillation column is recycled should be the reaction step or should be the evaporation step or a distillation step (e.g., the light ends-removing step, the dehydration step, or the heavy ends-removing step) positioned upstream from the distillation step associated with the distillation column.

The process liquid (e.g., the overhead liquid (including the aqueous phase and the organic phase separated in the decanter) of the distillation column in the at least one distillation step) to be recycled to the step satisfying the operating condition (v) preferably has an acetic acid concentration of 5 percent by mass or more (e.g., 10 percent by mass or more), more preferably 20 percent by mass or more (e.g., 30 percent by mass or more), further preferably 40 percent by mass or more (e.g., 50 percent by mass or more), particularly preferably 60 percent by mass or more (e.g., 70 percent by mass or more), and especially preferably 80 percent by mass or more (e.g., 90 percent by mass or more). The upper limit of the acetic acid concentration is preferably 99.999 percent by mass, and may be 99.99 percent by mass or 99.9 percent by mass. The process liquid to be recycled may be an overhead liquid of the distillation column in which the charge liquid has an acetic acid concentration within the above range.

EXAMPLES

Hereinafter, the present invention will be described in more detail with reference to Examples. However, the present invention is not intended to be limited by these Examples. "MeI" represents methyl iodide, "MA" represents methyl acetate, "LiI" represents lithium iodide, and "Rh" represents rhodium, respectively. In the compositional analysis of a liquid phase portion, a water concentration was measured by the Karl Fischer water determination method; a formic acid concentration was measured by liquid chromatography; a rhodium concentration was measured by ICP analysis (or atomic adsorption spectrometry); as for a lithium iodide concentration, Li was measured by ICP analysis, and iodine was measured by electrometric titration analysis; and concentrations of other components were measured by gas chromatography. The partial pressure of each gas component in a gas phase portion was calculated from total pressure and each gas component concentration measured by gas chromatography. The units "%" and "ppm" mean "percent by mass" and "ppm by mass", respectively.

Comparative Example 1

A 1000 ml zirconium autoclave was charged with MeI, MA, water, LiI, rhodium iodide (in the experiment, a complex catalyst ([$Rh(CO)_2I_2$]$^-$) (Rh concentration in the table is in terms of metal), and acetic acid in the ratios shown in Table 1 as an initial introduction composition. After displacement of air (holding at air atmospheric pressure), $H_2$, $CO_2$, CO, and air (nitrogen:oxygen (volume ratio)=80:20) were charged into the autoclave such that the $H_2$ partial pressure, $CO_2$ partial pressure, CO partial pressure, and $O_2$ concentration in the gas phase were respectively the partial pressures (absolute pressure) or percent by volume shown in Table 1. The mixture was held for 30 minutes with the temperature kept at 180° C. in an oil bath. The total pressure immediately after the temperature reached 180° C. was 5.5 MPaG, and the total pressure after 8 minutes dropped to 5.3 MPaG. After cooling, the liquid was sampled and subjected to a compositional analysis, from which the formic acid concentration was found to be 55 ppm. The MA concentration and the water concentration decreased to 2.3% and 1.6%, respectively. The reason for this are the overall results of the followings: MA reacts with water to produce methanol and acetic acid; the methanol produced in equilibrium with CO undergoes carbonylation, whereby CO and methanol are consumed and acetic acid is produced; a part of methanol undergoes dimerization, thereby forming dimethyl ether and water, and the like. In addition, although the amount of water decreases due to decomposition of MA, it also increases with the formation of dimethyl ether, and hence the change in concentration was small. There were no major other changes in the composition. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Comparative Example 2

An experiment was carried out in the same manner as Comparative Example 1, except that MeI, MA, water, LiI, rhodium iodide (in the experiment, a complex catalyst ([$Rh(CO)_2I_2$]$^-$) (Rh concentration in the table is in terms of metal), and acetic acid in the ratios shown in Table 1 were charged into the autoclave as an initial introduction composition, and $H_2$, $CO_2$, CO, and air were charged into the autoclave such that the $H_2$ partial pressure, $CO_2$ partial pressure, CO partial pressure, and $O_2$ concentration in the gas phase were respectively the partial pressures (absolute pressure) or percent by volume shown in Table 1. After cooling, the liquid was sampled and subjected to a compositional analysis, from which the formic acid concentration was found to be 48 ppm. The MA concentration and the water concentration decreased to 2.3% and 1.6%, respectively. The reasons for this are as explained in Comparative Example 1. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Comparative Example 3

An experiment was carried out in the same manner as Comparative Example 1, except that MeI, MA, water, LiI, rhodium iodide (in the experiment, a complex catalyst ([$Rh(CO)_2I_2$]$^-$) (Rh concentration in the table is in terms of metal), and acetic acid in the ratios shown in Table 1 were charged into the autoclave as an initial introduction composition, and $H_2$, $CO_2$, CO, and air were charged into the autoclave such that the $H_2$ partial pressure, $CO_2$ partial pressure, CO partial pressure, and $O_2$ concentration in the gas phase were respectively the partial pressures (absolute pressure) or percent by volume shown in Table 1. After cooling, the liquid was sampled and subjected to a compositional analysis, from which the formic acid concentration was found to be 51 ppm. The MA concentration and the water concentration decreased to 2.3% and 1.6%, respectively. The reasons for this are as explained in Comparative Example 1. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Comparative Example 4

An experiment was carried out in the same manner as Comparative Example 1, except that MeI, MA, water, LiI, rhodium iodide (in the experiment, a complex catalyst ([Rh(CO)$_2$I$_2$]$^-$) (Rh concentration in the table is in terms of metal), and acetic acid in the ratios shown in Table 1 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 1 and held for 30 minutes at a temperature of 150° C. After cooling, the liquid was sampled and subjected to a compositional analysis, from which the formic acid concentration was found to be 51 ppm. The results of the compositional analysis at the start of the experiment and at the end of the experiment are shown in the table below. Further, although the acetic acid concentration is denoted as being the balance other trace impurities of around 0.2% were also present, mainly dimethyl ether, methanol, and the like.

Comparative Example 5

An experiment was carried out in the same manner as Comparative Example 1, except that MeI, MA, water, formic acid, and acetic acid in the ratios shown in Table 1 were charged into the autoclave as an initial introduction composition, and He, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 1 and held for 30 minutes at a temperature of 110° C. After cooling, the liquid was sampled and subjected to a compositional analysis, from which the formic acid concentration was found to be 47 ppm. Since no catalyst was added, carbonylation did not occur and there was no fundamental change in the composition other than formic acid. The MA concentration slightly decreased and the water concentration hardly changed. The decrease in the MA concentration is thought to be the result of MA reacting with water to produce methanol and acetic acid, and a part of the produced methanol changing into dimethyl ether and producing water There were no major other changes in the composition. The total pressure immediately after the temperature reached 110° C. was 0.9 MPaG, and the total pressure at 110° C. when the experiment finished was the same, namely, 0.9 MPaG. Under the rhodium complex catalyst-containing conditions (Comparative Examples 1 to 3), because CO is consumed in the reaction and some H$_2$ and CO$_2$ is produced, the net result is a drop in pressure of about 0.1 to 0.5 MPa, but when the rhodium complex catalyst, is absent, since gas is not produced, it is considered that there is almost no drop in pressure. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Comparative Example 6

An experiment was carried out in the same manner as Comparative Example 5, except that MeI, MA, water, formic acid, and acetic acid in the ratios shown in Table 1 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 1. After cooling, the liquid was sampled and subjected to a compositional analysis, from which the formic acid concentration was found to be 42 ppm. The results of the compositional analysis at the start of the experiment and at the end of the experiment are shown in the table below. Further, although the acetic acid concentration is denoted as being the balance other trace impurities of around 0.2% were also present, mainly dimethyl ether, methanol, and the like.

Comparative Example 7

An experiment was carried out in the same manner as Comparative Example 5, except that MeI, MA, water, formic acid, and acetic acid in the ratios shown in Table 1 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 1. After cooling, the liquid was sampled and subjected to a compositional analysis, from which the formic acid concentration was found to be 45 ppm. The results of the compositional analysis at the start of the experiment and at the end of the experiment are shown in the table below. Further, although the acetic acid concentration is denoted as being the balance other trace impurities of around 0.2% were also present, mainly dimethyl ether, methanol, and the like.

Comparative Example 8

An experiment was carried out in the same manner as Comparative Example 5, except that MeI, MA, water, formic acid, and acetic acid in the ratios shown in Table 1 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 1 and held for 30 minutes at a temperature of 100° C. After cooling, the liquid was sampled and subjected to a compositional analysis, from which the formic acid concentration was found to be 48 ppm. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 1

An experiment was carried out in the same manner as Comparative Example 1, except that MeI, MA, water, LiI, rhodium iodide (in the experiment, a complex catalyst ([Rh(CO)$_2$I$_2$]$^-$) (Rh concentration in the table is in terms of metal), and acetic acid in the ratios shown in Table 2 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 2. After cooling, the liquid was sampled and subjected to a compositional analysis, from which the formic acid concentration was found to be 45 ppm. The MA concentration and the water concentration decreased to 2.2% and 1.6%, respectively. The reasons for this are as explained in Comparative Example 1. There were no major other changes in the composition. The total pressure immediately after the temperature reached 180° C. was 3.9 MPaG, and the total pressure when the experiment finished dropped to 3.4 MPaG. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 2

An experiment was carried out in the same manner as Example 1, except that MeI, MA, water, LiI, rhodium iodide (in the experiment, a complex catalyst ([Rh(CO)$_2$I$_2$]$^-$) (Rh concentration in the table is in terms of metal), and acetic acid in the ratios shown in Table 2 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 2. After cooling, the liquid was sampled and subjected to a compositional analysis, from which the formic acid concentration was found to be 21 ppm. The MA concentration and the water concentration decreased to 2.3% and 1.6%, respectively. The reasons for this are as explained in Comparative Example 1. There were no major other changes in the composition. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 3

An experiment was carried out in the same manner as Example 1, except that MeI, MA, water, LiI, rhodium iodide (in the experiment, a complex catalyst ([Rh(CO)$_2$I$_2$]$^-$) (Rh concentration in the table is in terms of metal), and acetic acid in the ratios shown in Table 2 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 2. After cooling, the liquid was sampled and subjected to a compositional analysis, from which the formic acid concentration was found to be 40 ppm. The MA concentration and the water concentration decreased to 2.3% and 1.6%, respectively. The reasons for this are as explained in Comparative Example 1. There were no major other changes in the composition. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 4

An experiment was carried out in the same manner as Example 1, except that the mixture was held for 30 minutes at a temperature of 188° C. After cooling, the liquid was sampled and subjected to a compositional analysis, from which the formic acid concentration was found to be 37 ppm. The MA concentration and the water concentration decreased to 2.0% and 1.4%, respectively. The reasons for this are as explained in Comparative Example 1. There were no major other changes in the composition. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 5

An experiment was carried out in the same manner as Example 1, except that MeI, MA, water, formic acid, and acetic acid in the ratios shown in Table 2 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 2 and held for 30 minutes at a temperature of 110° C. After cooling, the liquid was sampled and subjected to a compositional analysis, from which the formic acid concentration was found to be 38 ppm. Since no catalyst was added, carbonylation did not occur and there was no fundamental change in the composition other than formic acid. The total pressure immediately after the temperature reached 110° C. was 1.0 MPaG, and the total pressure at 110° C. when the experiment finished was the same, namely, 1.0 MPaG. Under the rhodium complex catalyst-containing conditions (Examples 1 to 4), because CO is consumed in the reaction and some H$_2$ and CO$_2$ is produced, the net result is a drop in pressure of about 0.5 to 0.7 MPa, but when the rhodium complex catalyst is absent, since gas is not produced, it is considered that there is almost no drop in pressure. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 6

An experiment was carried out in the same manner as Example 5, except that MeI, MA, water, formic acid, and acetic acid in the ratios shown in Table 2 were charged into the autoclave as an initial introduction composition, and H$_2$, CO$_2$, CO, and air were charged into the autoclave such that the H$_2$ partial pressure, CO$_2$ partial pressure, CO partial pressure, and O$_2$ concentration in the gas phase were respectively the partial pressures (absolute pressure) or percent by volume shown in Table 2. After cooling, the liquid was sampled and subjected to a compositional analysis, from which the formic acid concentration was found to be 37 ppm. Since no catalyst was added, carbonylation did not occur and there was no fundamental change in the composition other than formic acid. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 7

An experiment was carried out in the same manner as Example 5, except that water, formic acid, and acetic acid in the ratios shown in Table 2 were charged into the autoclave as an initial introduction composition, and $H_2$, $CO_2$, CO, and air were charged into the autoclave such that the $H_2$ partial pressure, $CO_2$ partial pressure, CO partial pressure, and $O_2$ concentration in the gas phase were respectively the partial pressures (absolute pressure) or percent by volume shown in Table 2. After cooling, the liquid was sampled and subjected to a compositional analysis, from which the formic acid concentration was found to be 35 ppm. Since no catalyst was added, carbonylation did not occur and there was no fundamental change in the composition other than formic acid. The results of the compositional analysis at the start of the experiment and at the end of the experiment are shown in the table below. Further, because MA was not present in Example 7, the sum of dimethyl ether and methanol after the experiment finished was less than 0.1%.

Example 8

An experiment was carried out in the same manner as Example 5, except that MeI, MA, water, formic acid, and acetic acid in the ratios shown in Table 2 were charged into the autoclave as an initial introduction composition and $H_2$, $CO_2$, CO, and air were charged into the autoclave such that the $H_2$ partial pressure, $CO_2$ partial pressure, CO partial pressure, and $O_2$ concentration in the gas phase were respectively the partial pressures (absolute pressure) or percent by volume shown in Table 2. After cooling, the liquid was sampled and subjected to a compositional analysis, from which the formic acid concentration was found to be 21 ppm. Since no catalyst was added, carbonylation did not occur and there was no fundamental change in the composition other than formic acid. The results of the compositional analysis at the start of the experiment and at the end of the experiment are shown in the table below. Further, although the acetic acid concentration is denoted as being the balance, other trace impurities of around 0.2% were also present, mainly dimethyl ether, methanol, and the like.

Example 9

An experiment was carried out in the same manner as Example 5, except that MeI, MA, water, LiI, rhodium iodide (in the experiment, a complex catalyst ($[Rh(CO)_2I_2]^-$) (Rh concentration in the table is in terms of metal), formic acid, and acetic acid in the ratios shown in Table 2 were charged into the autoclave as an initial introduction composition, and $H_2$, $CO_2$, CO, and air were charged into the autoclave such that the $H_2$ partial pressure, $CO_2$ partial pressure, CO partial pressure, and $O_2$ concentration in the gas phase were respectively the partial pressures (absolute pressure) or percent by volume shown in Table 2 and held for 10 minutes at a temperature of 145° C. After cooling, the liquid was sampled and subjected to a compositional analysis, from which the formic acid concentration was found to be 29 ppm. The results of the compositional analysis at the start of the experiment and at the end of the experiment are shown in the table below. Further, because the amount of MA in Example 9 was low, the sum of dimethyl ether and methanol after the experiment finished was about 0.1%.

The conditions and results of the comparative examples and examples are shown in Tables 1 and 2. In Tables 1 and 2, "PH2" represents the hydrogen partial pressure, "PCO2" represents the carbon dioxide partial pressure, "PCO" represents the carbon monoxide partial pressure, and "O2 in gas phase" represents the oxygen concentration in the gas phase. In the table, acetic acid concentration is denoted as being the "balance", but in actual fact, in some cases impurities such as the by-products described in the explanation of the reaction mixture were present in the sampling liquid in a total amount of 1 ppm to 1%.

TABLE 1

| | | Comparitive Example | | | | | | | |
|---|---|---|---|---|---|---|---|---|---|
| | | 1 | | 2 | | 3 | | 4 | |
| | | Start Time | Finish Time | Start Time | Finish Time | Start Time | Finish Time | Start Time | Finish Time |
| Formic Acid | ppm by mass | 0 | 55 | 0 | 48 | 0 | 51 | 0 | 51 |
| MeI | percent by mass | 10.1 | 9.7 | 10.0 | 9.7 | 9.8 | 9.7 | 9.9 | 9.7 |
| MA | percent by mass | 3.9 | 2.3 | 4.0 | 2.3 | 4.1 | 2.3 | 3.9 | 2.0 |
| Water | percent by mass | 2.1 | 1.6 | 2.0 | 1.6 | 2.1 | 1.6 | 1.8 | 1.7 |
| LiI | percent by mass | 15.1 | 14.9 | 14.9 | 14.9 | 15.0 | 14.9 | 15.2 | 15.0 |
| Rh | ppm by mass | 501 | 493 | 497 | 493 | 503 | 493 | 507 | 491 |
| Acetic Acid | percent by mass | balance | balance | balance | balance | balance | balance | balance | balance |
| Hexyl Iodide | ppb by mass | 0 | 93 | 0 | 93 | 0 | 98 | 0 | 5 |
| PH2 | kPa (absolute pressure) | 412 | 510 | 409 | 510 | 411 | 450 | 410 | 450 |
| PCO2 | kPa (absolute pressure) | 69 | 80 | 69 | 80 | 31 | 40 | 38 | 40 |
| PCO (Note) | MPa (absolute pressure) | 1.8 | 1.3 | 1.8 | 1.3 | 1.8 | 1.3 | 1.5 | 1.4 |
| O2 in Gas Phase | percent by volume | 7.7 | 7.5 | 6.9 | 6.8 | 7.7 | 7.5 | 6.9 | 6.8 |
| Temperature | ° C. | 180 | 180 | 180 | 180 | 180 | 180 | 150 | 150 |
| Retention Time | minutes | 30 | | 30 | | 30 | | 30 | |
| Formic Acid Concentration at Finish | ppm by mass | 55 | | 48 | | 51 | | 51 | |

TABLE 1-continued

| | | Comparitive Example | | | | | | | |
|---|---|---|---|---|---|---|---|---|---|
| | | 5 | | 6 | | 7 | | 8 | |
| | | Start Time | Finish Time | Start Time | Finish Time | Start Time | Finish Time | Start Time | Finish Time |
| Formic Acid | ppm by mass | 52 | 47 | 52 | 42 | 52 | 45 | 52 | 43 |
| MeI | percent by mass | 39 | 37 | 39 | 37 | 39 | 37 | 39 | 37 |
| MA | percent by mass | 5.5 | 5.2 | 5.5 | 5.3 | 5.5 | 5.3 | 5.5 | 5.2 |
| Water | percent by mass | 2.1 | 2.1 | 2.1 | 2.1 | 2.1 | 2.1 | 2.1 | 2.1 |
| LiI | percent by mass | 0 | 0 | 0 | 0 | 0 | 0 | 0 | 0 |
| Rh | ppm by mass | 0 | 0 | 0 | 0 | 0 | 0 | 0 | 0 |
| Acetic Acid | percent by mass | balance | balance | balance | balance | balance | balance | balance | balance |
| Hexyl Iodide | ppb by mass | 0 | 0 | 0 | 0 | 0 | 0 | 0 | 0 |
| PH2 | kPa (absolute pressure) | 5.5 | 5.5 | 5.7 | 5.5 | 5 | 4.9 | 5.1 | 4.9 |
| PCO2 | kPa (absolute pressure) | 23 | 22 | 24 | 22 | 19 | 18 | 18 | 18 |
| PCO (Note) | MPa (absolute pressure) | 15 | 15 | 15 | 15 | 15 | 15 | 15 | 15 |
| O2 in Gas Phase | percent by volume | 7.7 | 7.5 | 3.2 | 3 | 7.7 | 7.5 | 7.7 | 7.5 |
| Temperature | ° C. | 110 | 110 | 110 | 110 | 110 | 110 | 100 | 100 |
| Retention Time | minutes | 30 | | 30 | | 30 | | 30 | |
| Formic Acid Concentration at Finish | ppm by mass | 47 | | 42 | | 45 | | 48 | |

(Note)
Units of PCO in Comparative Examples 5 to 8 are kPa (absolute pressure).

TABLE 2

| | | Example | | | | | | | | | |
|---|---|---|---|---|---|---|---|---|---|---|---|
| | | 1 | | 2 | | 3 | | 4 | | 5 | |
| | | Start Time | Finish Time | Start Time | Finish Time | Start Time | Finish Time | Start Time | Finish Time | Start Time | Finish Time |
| Formic Acid | ppm by mass | 0 | 45 | 0 | 21 | 0 | 40 | 0 | 37 | 52 | 38 |
| MeI | percent by mass | 10.2 | 9.8 | 9.9 | 9.7 | 9.8 | 9.7 | 10.1 | 9.7 | 39 | 37 |
| MA | percent by mass | 4.2 | 2.2 | 4.1 | 2.3 | 4.1 | 2.3 | 3.9 | 2.0 | 5.5 | 5.2 |
| Water | percent by mass | 2.1 | 1.6 | 2.0 | 1.6 | 1.9 | 1.6 | 2.1 | 1.4 | 2.1 | 2.1 |
| LiI | percent by mass | 15.1 | 15.1 | 14.9 | 14.9 | 15.2 | 14.9 | 15 | 15.1 | 0 | 0 |
| Rh | ppm by mass | 505 | 495 | 498 | 493 | 502 | 493 | 499 | 491 | 0 | 0 |
| Acetic Acid | percent by mass | balance | balance | balance | balance | balance | balance | balance | balance | balance | balance |
| Hexyl Iodide | ppb by mass | 0 | 95 | 0 | 93 | 0 | 98 | 0 | 112 | 0 | 0 |
| PH2 | kPa (absolute pressure) | 410 | 450 | 11 | 50 | 409 | 440 | 410 | 450 | 5.1 | 4.9 |
| PCO2 | kPa (absolute pressure) | 31 | 40 | 11 | 20 | 29 | 40 | 29 | 41 | 19 | 18 |
| PCO (Note) | MPa (absolute pressure) | 1.8 | 1.3 | 1.8 | 1.3 | 1.8 | 1.3 | 1.8 | 1.1 | 15 | 15 |
| O2 in Gas Phase | percent by volume | 6.9 | 6.7 | 6.9 | 6.7 | 3.3 | 3.1 | 6.9 | 6.7 | 3.2 | 3 |
| Temperature | ° C. | 180 | 180 | 180 | 180 | 180 | 180 | 188 | 188 | 110 | 110 |
| Retention Time | minutes | 30 | | 30 | | 30 | | 30 | | 30 | |
| Formic Acid Concentration at Finish | ppm by mass | 45 | | 21 | | 40 | | 37 | | 38 | |

| | | Example | | | | | | | |
|---|---|---|---|---|---|---|---|---|---|
| | | 6 | | 7 | | 8 | | 9 | |
| | | Start Time | Finish Time | Start Time | Finish Time | Start Time | Finish Time | Start Time | Finish Time |
| Formic Acid | ppm by mass | 50 | 37 | 51 | 35 | 50 | 21 | 50 | 29 |
| MeI | percent by mass | 5.1 | 4.9 | 0 | 0 | 5.2 | 4.8 | 0.9 | 0.8 |
| MA | percent by mass | 4.9 | 4.7 | 0 | 0 | 5.2 | 4.9 | 1.1 | 0.9 |
| Water | percent by mass | 52 | 52 | 0.2 | 0.2 | 4.9 | 5.1 | 2 | 1.9 |

TABLE 2-continued

| | | | | | | | | | |
|---|---|---|---|---|---|---|---|---|---|
| LiI | percent by mass | 0 | 0 | 0 | 0 | 0 | 0 | 20 | 20 |
| Rh | ppm by mass | 0 | 0 | 0 | 0 | 0 | 0 | 670 | 650 |
| Acetic Acid | percent by mass | balance | balance | balance | balance | balance | balance | balance | balance |
| Hexyl Iodide | ppb by mass | 0 | 0 | 0 | 0 | 0 | 0 | 0 | 2 |
| PH2 | kPa (absolute pressure) | 5.2 | 4.8 | 1 | 0.9 | 4.7 | 4.5 | 0.4 | 0.5 |
| PCO2 | kPa (absolute pressure) | 19 | 18 | 11 | 10 | 2 | 2 | 0.4 | 0.5 |
| PCO (Note) | MPa (absolute pressure) | 10 | 10 | 10 | 10 | 4 | 4 | 0.01 | 0.004 |
| O2 in Gas Phase | percent by volume | 3.3 | 3.1 | 3.1 | 3 | 0.6 | 0.5 | 1.1 | 1 |
| Temperature | °C. | 110 | 110 | 110 | 110 | 150 | 150 | 145 | 145 |
| Retention Time | minutes | 30 | | 30 | | 30 | | 10 | |
| Formic Acid Concentration at Finish | ppm by mass | 37 | | 35 | | 21 | | 29 | |

(Note)
Units of PCO in Examples 5 to 9 are kPa (absolute pressure).

[Consideration of Results]

From a comparison of Comparative Example 1 and comparative Example 2, it can be seen that even when the hydrogen partial pressure is 500 kPa or more and the carbon dioxide partial pressure is 70 kPa or more, when the oxygen concentration in the gas phase is less than 7 percent by volume, the amount of formic acid that is produced decreases. From a comparison of Comparative Example 1 and Comparative Example 3, it can be seen that even when the oxygen concentration in the gas phase is 7 percent by volume or more, when the hydrogen partial pressure is less than 500 kPa and the carbon dioxide partial pressure is less than 70 kPa, the amount of formic acid that is produced decreases. However, from a comparison of Example 1 with Comparative Examples 1 to 4, it can be seen that by setting the hydrogen partial pressure to less than 500 kPa, the carbon dioxide partial pressure to less than 70 kPa, the temperature to more than 150° C., and the oxygen concentration in the gas phase to less than 7 percent by volume, the amount of formic acid that is produced decreases by a much larger amount than when only the hydrogen partial pressure is less than 500 kPa and the carbon dioxide partial pressure is less than 70 kPa or when only the oxygen concentration in the gas phase is less than 7 percent by volume. Further, from a comparison of Comparative Example 3 and Comparative Example 4, it can be seen that even when the temperature is raised from 150° C. to 180° C., when the oxygen concentration in the gas phase is 7 percent by volume or more, the amount of formic acid that is produced cannot be suppressed.

From a comparison of Comparative Example 5 and Comparative Example 6, it can be seen that even when the hydrogen partial pressure is more than 5 kPa and the carbon dioxide partial pressure is 20 kPa or more, when the oxygen concentration in the gas phase is less than 7 percent by volume, decomposition of formic acid is promoted. From a comparison of Comparative Example 5 and Comparative Example 7, it can be seen that even when the oxygen concentration in the gas phase is 7 percent by volume or more, when the hydrogen partial pressure is 5 kPa or less and the carbon dioxide partial pressure is less than 20 kPa, decomposition of formic acid is promoted. However, from a comparison of Example 6 with Comparative Examples 5 to 8, it can be seen that by setting the hydrogen partial pressure to 5 kPa or less, the carbon dioxide partial pressure to less than 20 kPa, the temperature to more than 100° C., and the oxygen concentration in the gas phase to less than 7 percent by volume, decomposition of formic acid is promoted much more than when only the hydrogen partial pressure is 5 kPa or less and the carbon dioxide partial pressure is less than 20 kPa or when only the oxygen concentration in the gas phase is less than 7 percent by volume. Further, from a comparison of Comparative Example 7 and comparative Example 8, it can be seen that even when the temperature is raised from 100° C. to 110° C., decomposition of formic acid is only slightly promoted.

From a comparison of Example 1 and Example 2, it can be seen that when the oxygen concentration in the gas phase is less than 7 percent by volume, the formation of formic acid is suppressed more the lower the hydrogen partial pressure and the carbon dioxide partial pressure are. Further, from a comparison of Example 1 and Example 3, it can be seen that when the hydrogen partial pressure is less than 500 kPa, the carbon dioxide partial pressure is less than 70 kPa, and the temperature is more than 150° C., the formation of formic acid is suppressed more the lower the oxygen concentration in the gas phase is. In addition, from a comparison of Example 1 and Example 4, it can be seen that when the hydrogen partial pressure is less than 500 kPa, the carbon dioxide partial pressure is less than 70 kPa, and the oxygen concentration in the gas phase is less than 7 percent by volume, the formation of formic acid is suppressed more the higher the temperature is.

From Examples 5 to 9, it can be seen that when the hydrogen partial pressure is 5 kPa or less, the carbon dioxide partial pressure is less than 20 kPa, the temperature is more than 100° C., and the oxygen concentration in the gas phase is less than 7 percent by volume, even if the composition, hydrogen partial pressure, carbon dioxide partial pressure, temperature, oxygen concentration in the gas phase, or retention time is different, decomposition of formic acid is promoted.

As a summary of the above description, configurations of the present invention, as well as variations thereof, will be described below as appendices

[1] A method for producing acetic acid, comprising at least one step selected from a step that satisfies the following operating condition (i) and a step that satisfies the following operating condition (ii) in an acetic acid production process, and controlling an oxygen concentration in an embodiment satisfying at least one selected from the following (iii) and (iv) for one or more processes:

(i) operating conditions involving a hydrogen partial pressure of less than 500 kPa (absolute pressure) a carbon dioxide partial pressure of less than 70 kPa (absolute pressure), and an operating temperature of more than 150° C. (preferably more than 175° C.);

(ii) operating conditions involving a hydrogen partial pressure of 5 kPa or less (absolute pressure), a carbon dioxide partial pressure of less than 20 kPa (absolute pressure), and an operating temperature of more than 100° C.;

(iii) the oxygen concentration in a gas phase is less than 7 percent by volume; and (iv) the oxygen concentration in a liquid phase is less than $7 \times 10^{-5}$ g/g.

[2] The method for producing acetic acid according to [1], wherein in the above (ii) the hydrogen partial pressure is 1 kPa (absolute pressure) or less and the carbon dioxide partial pressure is less than 2 kPa (absolute pressure).

[3] The method for producing acetic acid according to [1] or [2], wherein the method has a reaction step that satisfies the operating condition (i).

[4] The method for producing acetic acid according to [3], wherein a liquid reaction mixture in the reaction step has an acetic acid concentration of 30 mass present or more and a formic acid concentration of 102 ppm by mass or less.

[5] The method for producing acetic acid according to [3] or [4], wherein a liquid reaction mixture in the reaction step has an acetic acid concentration of 50 to 90 percent by mass, a metal catalyst concentration (in terms of metal) of 200 to 10000 ppm by mass, a methyl iodide concentration of 1 to 20 percent by mass, an ionic iodide concentration of 1 to 25 percent by mass, a water concentration of 0.1 to 15 percent by mass, a methyl acetate concentration of 0.1 to 30 percent by mass, and a formic acid concentration of 102 ppm by mass or less.

[6] The method for producing acetic acid according to any one of [1] to [5], wherein the method has an evaporation step or a distillation step that satisfies the operating condition (ii).

[7] The method for producing acetic acid according to [6], wherein a charge liquid to an evaporator in the evaporation step has an acetic acid concentration of 50 to 90 percent by mass, a metal catalyst concentration (in terms of metal) of 200 to 10000 ppm by mass, a methyl iodide concentration of 1 to 20 percent by mass, an ionic iodide concentration of 1 to 25 percent by mass, a water concentration of 0.1 to 15 percent by mass, a methyl acetate concentration of 0.1 to 30 percent by mass, and a formic acid concentration of 10000 ppm by mass or less.

[8] The method for producing acetic acid according to [6], wherein a charge liquid to the distillation column in the distillation step has an acetic acid concentration of 30 mass present or more and a formic acid concentration of 5 ppm by mass or more.

[9] The method for producing acetic acid according to [6], wherein a charge liquid to a distillation column in the distillation step has an acetic acid concentration of 40 to 85 percent by mass, a methyl iodide concentration of 2 to 50 percent by mass, a water concentration of 0.2 to 20 percent by mass, a methyl acetate concentration of 0.2 to 50 percent by mass, and a formic acid concentration of 5 to 10000 ppm by mass.

[10] The method for producing acetic acid according to [6], wherein a charge liquid to a distillation column in the distillation step has an acetic acid concentration of 80 to 99.9 percent by mass, a methyl iodide concentration of 0.01 to 16 percent by mass, a water concentration of 0.05 to 18 percent by mass, a methyl acetate concentration of 0.01 to 16 percent by mass, and a formic acid concentration of 5 to 10000 ppm by mass.

[11] The method for producing acetic acid according to [6], wherein a charge liquid to a distillation column in the distillation step has an acetic acid concentration of 99.1 to 99.999 percent by mass and a formic acid concentration of 5 to 9000 ppm by mass.

[12] The method for producing acetic acid according to any one of [1] to [11], wherein the gas phase in the above (iii) comprises at least one kind selected from the group consisting of acetic acid, methyl acetate, methanol, water, acetaldehyde, a by-product derived from acetaldehyde, and dialkyl ether, the by-product comprising at least one kind selected from the group consisting of alkyl iodides having 2 or more carbon atoms, alkanals having 4 or more carbon atoms, alkane carboxylic acids having 3 or more carbon atoms, alkanes, and ketones, and the dialkyl ether comprises at least dimethyl ether.

[13] The method for producing acetic acid according to any one of [1] to [12], wherein the method controls the oxygen concentration in an embodiment satisfying at least one selected from the following (iii-1) and (iv-1) for one or more processes:

(iii-1) the oxygen concentration in a gas phase is 5 percent by volume or less; and (iv-1) the oxygen concentration in a liquid phase is less than $2 \times 10^{-5}$ g/g.

[14] The method for producing acetic acid according to any one of [1] to [13], wherein a ratio of oxygen to carbon monoxide in the gas phase in the above (iii) is 2 percent by volume or less (preferably 1 percent by volume or less) and/or the ratio of oxygen to carbon monoxide in the liquid phase in the above (iv) is 2 percent by volume or less (preferably 1 percent by volume or less).

[15] The method for producing acetic acid according to any one of [1] to [14], wherein in the above (iii) and/or (iv), at least one component selected from the group consisting of an oxygen-containing gas, an oxygen-containing compound, and an oxygen generating agent is introduced to be the oxygen concentration in the gas phase in the above (iii) of 1 ppt by volume or more (preferably 1 ppb by volume or more) and/or the oxygen concentration in the liquid phase in the above (iv) of $0.1 \times 10^{-9}$ g/g or more.

[16] The method for producing acetic acid according to any one of [1] to [15], wherein in the above (iii) and/or (iv), the oxygen concentration is a concentration of 0.25 mol or less with respect to a total of 1 mol of hydrogen iodide and methyl iodide.

[17] The method for producing acetic acid according to any one of [1] to [16], wherein the gas phase in the above (iii) and/or the liquid phase in the above (iv) is a gas phase and/or a liquid phase in the reaction step, the evaporation step, or the distillation step.

[18] The method for producing acetic acid according to any one of [1] to [17], wherein the acetic acid production process has a carbonylation step of reacting methanol with carbon monoxide to produce acetic acid, an evaporation step of separating the reaction mixture obtained in the carbonylation step into a vapor stream and a residue stream, and a light ends-removing step of separating the vapor stream into an overhead stream rich in light ends and a first acetic acid stream rich in acetic acid by subjecting the vapor stream to distillation, or in addition to these steps, further comprises at least one step from among the following (a) to (d):

(a) a dehydration step of separating the first acetic acid stream by distillation into an overhead stream rich in water and a second acetic acid stream more enriched with acetic acid than the first acetic acid stream;
(b) a heavy ends-removing step of separating the first or the second acetic acid stream by distillation into a bottoms stream rich in heavy ends and a third acetic acid stream more enriched with acetic acid than the acetic acid stream before being subjected to distillation;
(c) an adsorptive removing step of treating the first, second, or third acetic acid stream with an ion exchange resin to obtain a fourth acetic acid stream; and
(d) a product step of distilling the first, second, third, or fourth acetic acid stream to obtain a fifth acetic acid stream more enriched with acetic acid than the acetic acid streams before being subjected to distillation.
[19] The method for producing acetic acid according to [18], wherein the carbonylation step satisfies the operating condition (i).
[20] The method for producing acetic acid according to [18] or [19], wherein at least one step selected from the evaporation step, the light ends-removing step, the dehydration step, the heavy ends-removing step, and the product step satisfies the operating condition (ii).
[21] The method for producing acetic acid according to any one of [18] to [20], wherein the gas phase and/or the liquid phase in at least one step selected from the carbonylation step, the evaporation step, the light ends-removing step, the dehydration step, the heavy ends-removing step, and the product step is a gas phase in the above (iii) and/or a liquid phase in the above (iv).
[22] The method for producing acetic acid according to any one of [1] to [21], wherein a retention time in the step that satisfies the operating condition (i) or the step that satisfies the operating condition (ii) is 1 minute or more (e.g., not less than 10 minutes and not more than 2 hours).
[23] The method for producing acetic acid according to any one of [1] to [22], wherein a process liquid having a formic acid concentration of 10 ppm by mass or more is recycled to a step that satisfies operating conditions involving a hydrogen partial pressure of less than 500 kPa (absolute pressure), a carbon dioxide partial pressure of less than 70 kPa (absolute pressure), and an operating temperature of more than 100° C.
[24] The method for producing acetic acid according to [23], wherein the process liquid to be recycled has an acetic acid concentration of 5 percent by mass or more (e.g., 5 to 99.999 percent by mass).
[25] The method for producing acetic acid according to any one of [1] to [24], wherein the acetic acid production process has at least one distillation step, and an overhead liquid of a distillation column in the at least one distillation step is recycled to the step that satisfies the operating condition (i) and/or the step that satisfies the operating condition (ii).
[26] The method for producing acetic acid according to [25], wherein the step to which the overhead liquid of a distillation column is recycled is the reaction step and/or the evaporation step or a distillation step positioned upstream from the distillation step associated with the distillation column.
[27] The method for producing acetic acid according to [25] or [26], wherein the overhead liquid of a distillation column has an acetic acid concentration of 5 percent by mass or more (e.g., 80 to 99.999 percent by mass).
[28] The method for producing acetic acid according to any one of [25] to [27], wherein the overhead liquid of a distillation column has an acetic acid concentration in the charge liquid of 80 percent by mass or more (e.g., 80 to 99.999 percent by mass).
[29] The method for producing acetic acid according to any one of [1] to [28], wherein in the above (i) the hydrogen partial pressure is 1 to 150 kPa (absolute pressure) or less, the carbon dioxide partial pressure is less than 70 kPa (absolute pressure), and the operating temperature is more than 175° C. and not more than 250° C.
[30] The method for producing acetic acid according to any one of [1] to [29], wherein in the above (ii) the carbon dioxide partial pressure is 12 kPa (absolute pressure) or less and the operating temperature is 106 to 250° C.

INDUSTRIAL APPLICABILITY

According to the present invention, the formic acid concentration in an acetic acid product can be lowered by simple approach.

REFERENCE SIGNS LIST 1 reactor
2 evaporator
3, 5, 6 distillation column
4 decanter
7 ion exchange resin column
8 scrubber system
5 acetaldehyde separation and removal system
16 reaction mixture feed line
17 vapor stream discharge line
18, 19 residue stream recycling line
54 carbon monoxide-containing gas introducing line
55, 56 potassium hydroxide introducing line
57 catalyst-circulating pump
91 distillation column (first acetaldehyde-removing column)
92 extraction column
93 distillation column (second acetaldehyde-removing column)
94 distillation column (extractive distillation column)
95 decanter
96 decanter
97 distillation column (acetaldehyde-removing column)
98 distillation column (extractive distillation column)
99 decanter
200 chimney tray

The invention claimed is:
1. A method for producing acetic acid, comprising a carbonylation step of reacting methanol and carbon monoxide to produce acetic acid, an evaporation step of separating the reaction mixture obtained in the carbonylation step into a vapor stream and a residue stream in an evaporator, and a light ends-removing step of subjecting the vapor stream to distillation to separate the vapor stream into at least two streams comprising an overhead stream rich in light ends and a first acetic acid stream rich in acetic acid,
in addition to these steps, the method further may comprise at least one step from among the following (a) to (d);
(a) a dehydration step of separating the first acetic acid stream by distillation into an overhead stream rich in water and a second acetic acid stream more enriched with acetic acid than the first acetic acid stream;
(b) a heavy ends-removing step of separating the first or the second acetic acid stream by distillation into a bottom stream rich in heavy ends and a third acetic acid stream more enriched with acetic acid than the acetic acid stream before being subjected to distillation;

(c) an adsorptive removing step of treating the first, second, or third acetic acid stream with an ion exchange resin to obtain a fourth acetic acid stream; and (d) a product step of distilling the first, second, third, or fourth acetic acid stream to obtain a fifth acetic acid stream more enriched with acetic acid than the acetic acid streams before being subjected to distillation, wherein the method for producing acetic acid may comprise, in place of the evaporation step and the light ends-removing step, an evaporative light ends-removing step of separating the reaction mixture obtained in the carbonylation step into a stream containing the metal catalyst, an overhead stream rich in the light ends, and a first acetic acid stream rich in acetic acid, the method may comprise, instead of the light ends-removing step and the dehydration step, a light ends-water-removing step which is a light ends-removing step also having the function of the dehydration step in which the vapor stream is subjected to distillation and separated into an overhead stream rich in light ends and an acetic acid stream dehydrated to a water concentration equivalent to that of the second acetic acid stream, and the evaporative light ends-removing step may be an evaporative light ends-water-removing step also having the function of the dehydration step, and wherein (1) the carbonylation step satisfies the following operating condition (i) in an acetic acid production process and satisfies the operating condition (iii) and/or (iv), and (2) the evaporation step and/or at least one distillation step selected from the group consisting of the light ends-removing step, the dehydration step, the heavy ends-removing step, the product step, the evaporative light ends-removing step, the light ends-water-removing step, and the evaporative light ends-water-removing step satisfies the following operating condition (ii) in an acetic acid production process and satisfies the operating conditions (iii) and/or (iv):

(i) operating conditions involving a hydrogen partial pressure of less than 500 kPa (absolute pressure), a carbon dioxide partial pressure of less than 60 kPa (absolute pressure), and an operating temperature of more than 150° C.;

(ii) operating conditions involving a hydrogen partial pressure of 5 kPa or less (absolute pressure), a carbon dioxide partial pressure of less than 20 kPa (absolute pressure), and an operating temperature of more than 100° C.;

(iii) the oxygen concentration in a gas phase is less than 7 percent by volume; and (iv) the oxygen concentration in a liquid phase is less than $7 \times 10^{-5}$ g/g.

2. The method for producing acetic acid according to claim 1, wherein the method has a reaction step that satisfies the operating condition (i).

3. The method for producing acetic acid according to claim 2, wherein a liquid reaction mixture in the reaction step has an acetic acid concentration of 50 to 90 percent by mass, a metal catalyst concentration (in terms of metal) of 200 to 10000 ppm by mass, a methyl iodide concentration of 1 to 20 percent by mass, an ionic iodide concentration of 1 to 25 percent by mass, a water concentration of 0.1 to 15 percent by mass, a methyl acetate concentration of 0.1 to 30 percent by mass, and a formic acid concentration of 102 ppm by mass or less.

4. The method for producing acetic acid according to claim 1, wherein the method has an evaporation step or a distillation step that satisfies the operating condition (ii).

5. The method for producing acetic acid according to claim 4, wherein a charge liquid to an evaporator in the evaporation step has an acetic acid concentration of 50 to 90 percent by mass, a metal catalyst concentration (in terms of metal) of 200 to 10000 ppm by mass, a methyl iodide concentration of 1 to 20 percent by mass, an ionic iodide concentration of 1 to 25 percent by mass, a water concentration of 0.1 to 15 percent by mass, a methyl acetate concentration of 0.1 to 30 percent by mass, and a formic acid concentration of 10000 ppm by mass or less.

6. The method for producing acetic acid according to claim 4, wherein a charge liquid to a distillation column in the distillation step has an acetic acid concentration of 40 to 85 percent by mass, a methyl iodide concentration of 2 to 50 percent by mass, a water concentration of 0.2 to 20 percent by mass, a methyl acetate concentration of 0.2 to 50 percent by mass, and a formic acid concentration of 5 to 10000 ppm by mass.

7. The method for producing acetic acid according to claim 4, wherein a charge liquid to a distillation column in the distillation step has an acetic acid concentration of 80 to 99.9 percent by mass, a methyl iodide concentration of 0.01 to 16 percent by mass, a water concentration of 0.05 to 18 percent by mass, a methyl acetate concentration of 0.01 to 16 percent by mass, and a formic acid concentration of 5 to 10000 ppm by mass.

8. The method for producing acetic acid according to claim 4, wherein a charge liquid to a distillation column in the distillation step has an acetic acid concentration of 99.1 to 99.999 percent by mass and a formic acid concentration of 5 to 9000 ppm by mass.

9. The method for producing acetic acid according to claim 1, wherein a ratio of oxygen to carbon monoxide in the gas phase in the (iii) is 2 percent by volume or less and/or the ratio of oxygen to carbon monoxide in the liquid phase in the (iv) is 2 percent by volume or less.

10. The method for producing acetic acid according to claim 1, wherein in the (iii) and/or the (iv), at least one component selected from the group consisting of an oxygen-containing gas, an oxygen-containing compound, and an oxygen generating agent is introduced to be the oxygen concentration in the gas phase in the (iii) of 1 ppt by volume or more and/or the oxygen concentration in the liquid phase in the (iv) of $0.1 \times 10^{-9}$ g/g or more.

11. The method for producing acetic acid according to claim 1, wherein in the (iii) and/or the (iv), the oxygen concentration is a concentration of 0.25 mol or less with respect to a total of 1 mol of hydrogen iodide and methyl iodide.

12. The method for producing acetic acid according to claim 1, wherein the gas phase in the (iii) and/or the liquid phase in the (iv) is a gas phase and/or a liquid phase in the reaction step, the evaporation step, or the distillation step.

13. The method for producing acetic acid according to claim 1, wherein the acetic acid production process has a carbonylation step of reacting methanol with carbon monoxide to produce acetic acid, an evaporation step of separating the reaction mixture obtained in the carbonylation step into a vapor stream and a residue stream, and a light ends-removing step of separating the vapor stream into at least two streams comprising an overhead stream rich in light ends and a first acetic acid stream rich in acetic acid by subjecting the vapor stream to distillation, or in addition to these steps, further comprises at least one step from among the following (a) to (d):

(a) a dehydration step of separating the first acetic acid stream by distillation into an overhead stream rich in water and a second acetic acid stream more enriched with acetic acid than the first acetic acid stream;

(b) a heavy ends-removing step of separating the first or the second acetic acid stream by distillation into a bottoms stream rich in heavy ends and a third acetic acid stream more enriched with acetic acid than the acetic acid stream before being subjected to distillation;

(c) an adsorptive removing step of treating the first, second, or third acetic acid stream with an ion exchange resin to obtain a fourth acetic acid stream; and (d) a product step of distilling the first, second, third, or fourth acetic acid stream to obtain a fifth acetic acid stream more enriched with acetic acid than the acetic acid streams before being subjected to distillation.

14. The method for producing acetic acid according to claim 13, wherein the carbonylation step satisfies the operating condition (i).

15. The method for producing acetic acid according to claim 13, wherein at least one step selected from the evaporation step, the light ends-removing step, the dehydration step, the heavy ends-removing step, and the product step satisfies the operating condition (ii).

16. The method for producing acetic acid according to claim 13, wherein the gas phase and/or the liquid phase in at least one step selected from the carbonylation step, the evaporation step, the light ends-removing step, the dehydration step, the heavy ends-removing step, and the product step is a gas phase in the (iii) and/or a liquid phase in the (iv).

17. The method for producing acetic acid according to claim 1, wherein a retention time in the (1) carbonylation step or the (2) evaporation step and/or the at least one distillation step is 1 minute or more.

18. The method for producing acetic acid according to claim 1, wherein a process liquid having a formic acid concentration of 10 ppm by mass or more is recycled to a step that satisfies operating conditions involving a hydrogen partial pressure of less than 500 kPa (absolute pressure), a carbon dioxide partial pressure of less than 70 kPa (absolute pressure), and an operating temperature of more than 100° C.

19. The method for producing acetic acid according to claim 1, wherein the acetic acid production process has at least one distillation step, and an overhead liquid of a distillation column in the at least one distillation step is recycled to the step that satisfies the operating condition (i) and/or the step that satisfies the operating condition (ii).

20. The method for producing acetic acid according to claim 19, wherein the step to which the overhead liquid of a distillation column is recycled is the reaction step and/or the evaporation step or a distillation step positioned upstream from the distillation step associated with the distillation column.

21. The method for producing acetic acid according to claim 1, wherein the light ends-removing step separates the vapor stream into the overhead stream, the first acetic acid stream, and a bottom stream.

22. The method for producing acetic acid according to claim 13, wherein the light ends-removing step separates the vapor stream into the overhead stream, the first acetic acid stream, and a bottom stream.

* * * * *